(12) United States Patent
Ledet et al.

(10) Patent No.: US 12,733,958 B2
(45) Date of Patent: Sep. 15, 2026

(54) IMPLANTABLE SCREW AND METHODS FOR USE

(71) Applicant: RENSSELAER POLYTECHNIC INSTITUTE, Troy, NY (US)

(72) Inventors: Eric Howard Ledet, Schenectady, NY (US); Kate Ronin, Brooklyn, NY (US); Erin Mahoney, New Hartford, CT (US); Sydney Breaux, Fairfax, VA (US); Ryleigh Greenwald, Piscataway, NJ (US); Garrett Volley, Glenwood, MD (US); Derek Nelson, Troy, NY (US)

(73) Assignee: RENSSELAER POLYTECHNIC INSTITUTE, Troy, NY (US)

( * ) Notice: Subject to any disclaimer, the term of this patent is extended or adjusted under 35 U.S.C. 154(b) by 0 days.

(21) Appl. No.: 18/927,500

(22) Filed: Oct. 25, 2024

(65) Prior Publication Data

US 2025/0120748 A1 Apr. 17, 2025

Related U.S. Application Data

(63) Continuation of application No. PCT/US2023/066263, filed on Apr. 26, 2023.

(60) Provisional application No. 63/334,772, filed on Apr. 26, 2022.

(51) Int. Cl.

| | |
|---|---|
| ***A61B 17/70*** | (2006.01) |
| ***A61B 17/86*** | (2006.01) |
| ***F16B 35/04*** | (2006.01) |

(52) U.S. Cl.
CPC ...... *A61B 17/7002* (2013.01); *A61B 17/7032* (2013.01); *A61B 17/866* (2013.01); *F16B 35/048* (2013.01)

(58) Field of Classification Search
CPC .............. A61B 17/701; A61B 17/7019; A61B 17/7026; A61B 17/7031; A61B 17/8625; A61B 17/8605
See application file for complete search history.

(56) References Cited

U.S. PATENT DOCUMENTS 4,959,064 A * 9/1990 Engelhardt ............. B23P 13/00 606/65
6,656,184 B1 * 12/2003 White ................ A61B 17/8625 606/318

(Continued)

OTHER PUBLICATIONS

International Search Report and Written Opinion of the International Searching Authority for PCT/US2023/066263, Nov. 21, 2023, 16 pages.

*Primary Examiner* — Matthew J Lawson
(74) *Attorney, Agent, or Firm* — Heslin Rothenberg Farley & Mesiti P.C.; Jacquelyn A. Graff, Esq.

(57) ABSTRACT

Implantable screws, implants, and systems that provide load-sharing while assisting with stabilization of the spine. The implantable screws including a proximal section, a distal section, and a middle section with two members coupling the proximal section and the distal section. The implantable screws may be used by applying a physiological load onto the first implantable screw and the second implantable screw to flex a middle section of each implantable screw and displace a proximal section relative to a distal section of each implantable screw.

23 Claims, 29 Drawing Sheets

(56) References Cited

U.S. PATENT DOCUMENTS

| | | | | |
|---|---|---|---|---|
| 7,175,626 | B2 * | 2/2007 | Neff | A61B 17/8875 606/86 A |
| 2002/0198527 | A1 | 12/2002 | Muckter | |
| 2005/0143823 | A1 * | 6/2005 | Boyd | A61B 17/8685 606/279 |
| 2005/0154390 | A1 * | 7/2005 | Biedermann | A61B 17/7028 606/279 |
| 2009/0157123 | A1 * | 6/2009 | Appenzeller | A61B 17/8685 606/301 |
| 2009/0264937 | A1 * | 10/2009 | Parrott | A61B 17/8625 606/301 |
| 2011/0257687 | A1 | 10/2011 | Trieu | |
| 2016/0317204 | A1 | 11/2016 | Appenzeller | |
| 2018/0263674 | A1 * | 9/2018 | Brianza | A61B 17/8605 |
| 2022/0218400 | A1 * | 7/2022 | Krumme | A61B 17/844 |
| 2024/0000484 | A1 * | 1/2024 | Tsuang | A61B 17/7001 |

* cited by examiner

IMPLANTABLE SCREW AND METHODS FOR USE

CROSS REFERENCE TO RELATED APPLICATION

This application is a continuation of PCT/US2023/066263 filed Apr. 26, 2023 and entitled Implantable Screw and Methods for Use, which claims priority benefit under 35 U.S.C. § 119(e) of U.S. provisional application No. 63/334,772 filed Apr. 26, 2022, which are incorporated herein by reference in their entireties.

FIELD OF THE INVENTION

The present disclosure relates generally to general surgery, orthopaedic and neurosurgical implants used for insertion into at least one bone segments of a patient. More specifically, but not exclusively, the present disclosure concerns implantable screws, systems and methods of using the same.

BACKGROUND OF THE INVENTION

The present disclosure generally relates to implants and methods that provide structural support to aspects of a spine, and in particular to implantable screws and related methods that can assist with stabilization of the spine.

Many spinal disorders use screws and rods for realigning the vertebrae of a patient's spine. The screws include tulip heads rigidly fixed to the threaded shafts. Other known screws include a dynamic portion providing for motion in one direction.

Many of these screws are provide rigid fixation that stress-shields bone. Existing systems do not provide load-sharing. As a result, a need exists for implants and methods that overcome one or more of the above-noted deficiencies of existing implants.

SUMMARY OF THE INVENTION

Aspects of the present disclosure provide screws, systems and methods of using the same.

In one aspect, the present disclosure provides an implantable screw including a head portion, a shaft, and a middle portion coupling the head portion to the shaft. The middle portion including a first member coupled to and extending between a first side of the head portion and the shaft and a second member coupled to and extending between a second side of the head portion and the shaft.

In another aspect, provided herein is a method for using at least one implantable screw includes inserting a first implantable screw into a first vertebrae and inserting a second implantable screw into a second vertebrae. The method also includes attaching a rod into the first implantable screw and the second implantable screw. The method further includes applying a physiological load onto the first implantable screw and the second implantable screw to flex a middle section of each implantable screw and displace a proximal section relative to a distal section of each implantable screw.

These, and other objects, features and advantages of this disclosure will become apparent from the following detailed description of the various aspects of the disclosure taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion.

DETAILED DESCRIPTION FOR CARRYING OUT THE INVENTION

Generally stated, disclosed herein are implantable screws, implants, and systems. Further, surgical methods for inserting the implantable screws are discussed.

In this detailed description and the following claims, the words proximal, distal, anterior, posterior, medial, lateral, superior, inferior, cephalad and caudally are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the implant, "posterior" means a direction towards the back side of the implant, "medial" means towards the midline of the implant, "lateral" is a direction towards the sides or away from the midline of the implant, "superior" means a direction above and "inferior" means a direction below another object or structure, "cephalad" means a direction toward the head and "caudally" means a direction toward the inferior part of the body.

Similarly, positions or directions may be used herein with reference to anatomical structures or surfaces. For example, as the current devices and methods are described herein with reference to use with the bones of the spine, the bones of the spine may be used to describe the surfaces, positions, directions or orientations of the devices, instrumentation and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the device and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices and methods, and the aspects, components, features and the like thereof, described herein with respect to a right side of the spine may be mirrored so that they likewise function with a left side of the spine and vice versa.

Figures 1, 2:
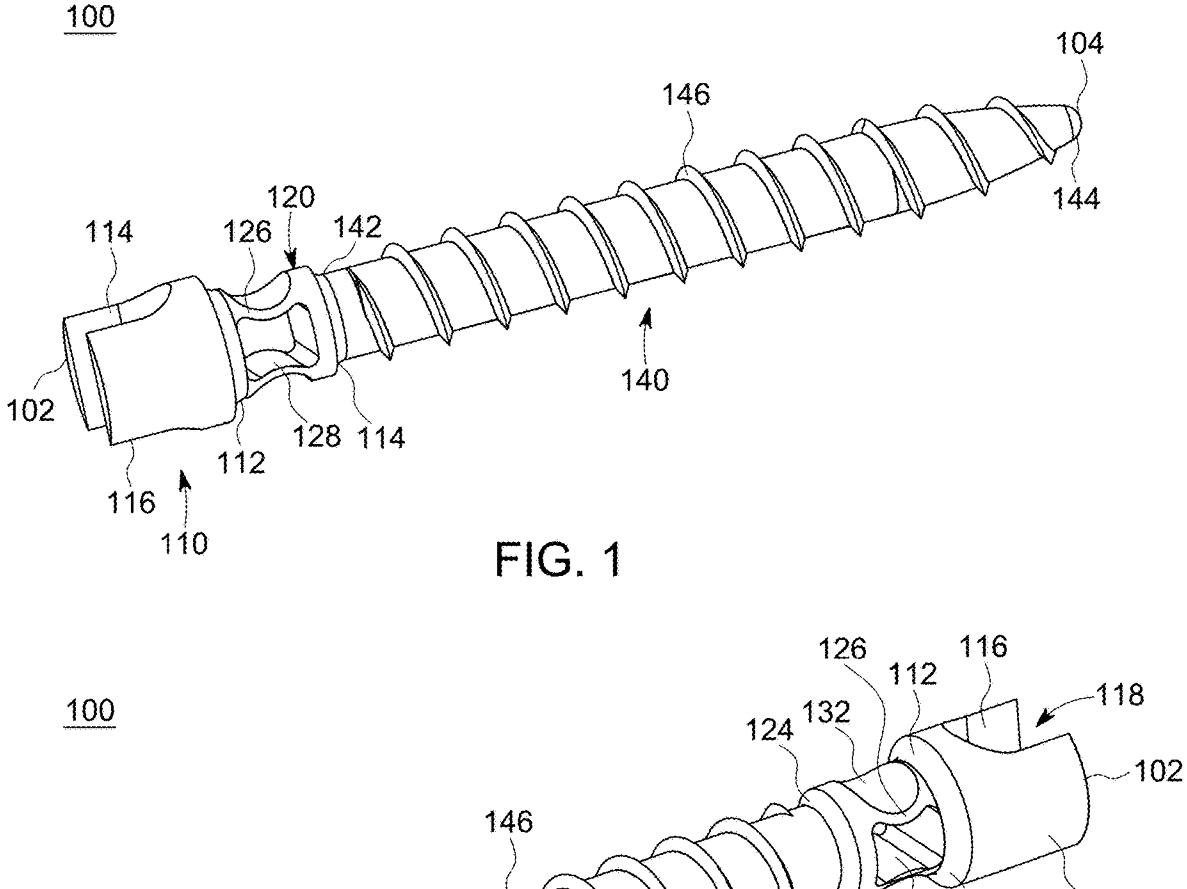
FIG. 1 is a first perspective view of an implantable screw, in accordance with an aspect of the present disclosure.
FIG. 2 is a second perspective view of the implantable screw of FIG. 1, in accordance with an aspect of the present disclosure.
Figure 3:
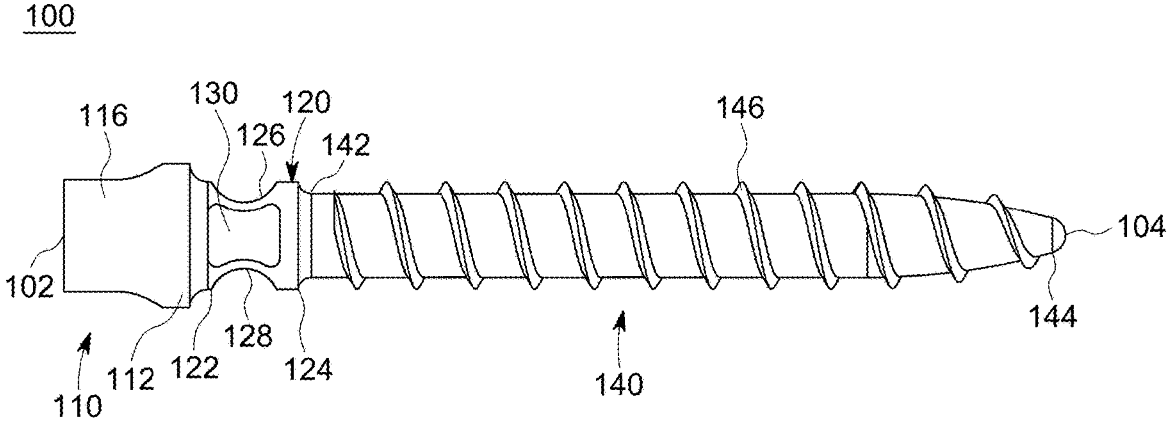
FIG. 3 is a first side view of the implantable screw of FIG. 1, in accordance with an aspect of the present disclosure.
Figure 4:
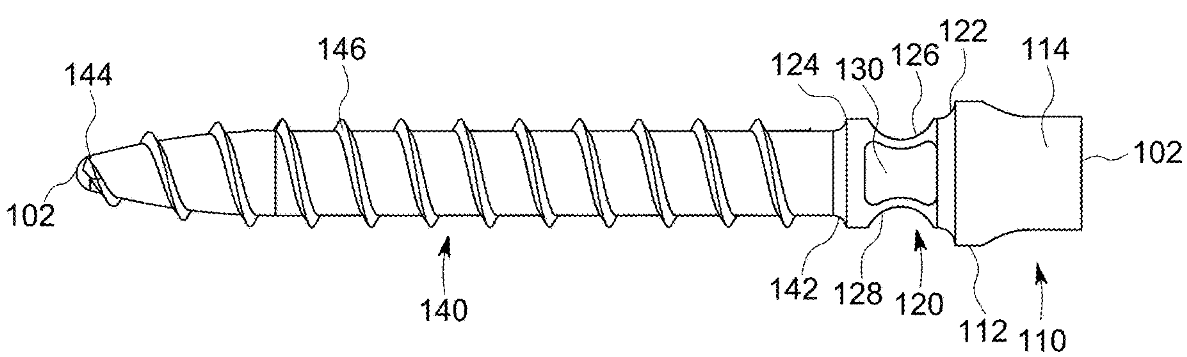
FIG. 4 is a second side view of the implantable screw of FIG. 1, in accordance with an aspect of the present disclosure.
Figure 5:
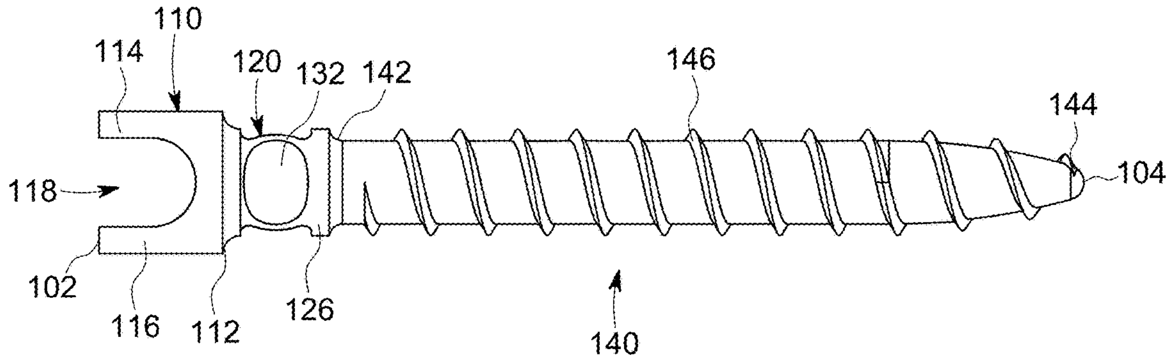
FIG. 5 is a first end view of the implantable screw of FIG. 1, in accordance with an aspect of the present disclosure.
Figure 6:
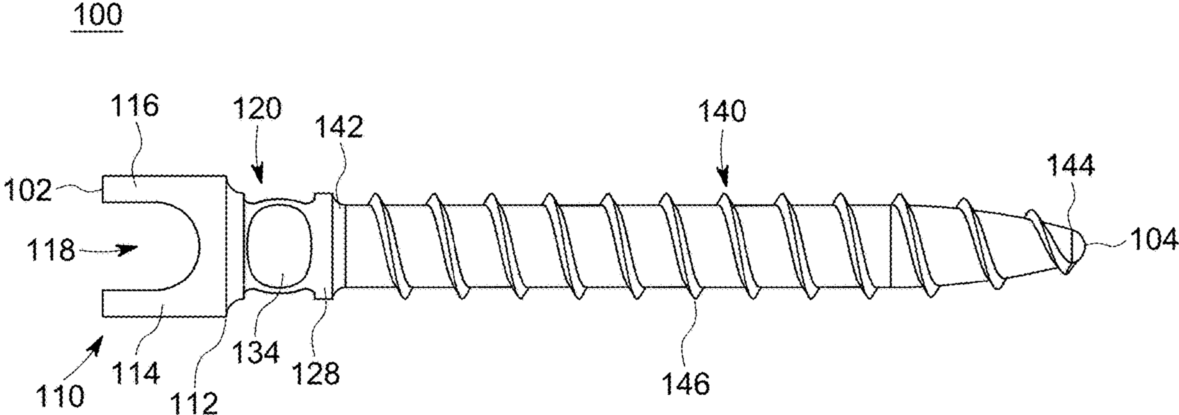
FIG. 6 is a second end view of the implantable screw of FIG. 1, in accordance with an aspect of the present disclosure.
Figure 7:
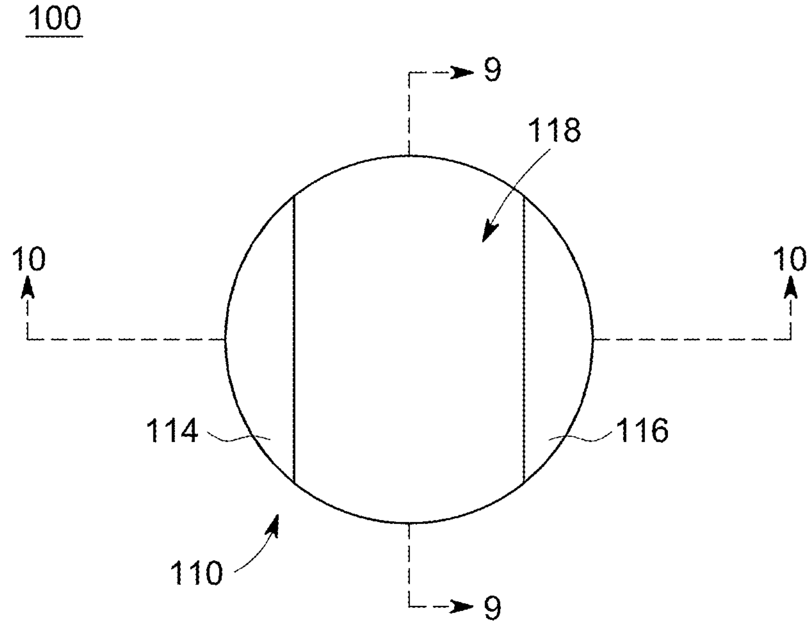
FIG. 7 is a top view of the implantable screw of FIG. 1, in accordance with an aspect of the present disclosure.
Figure 8:
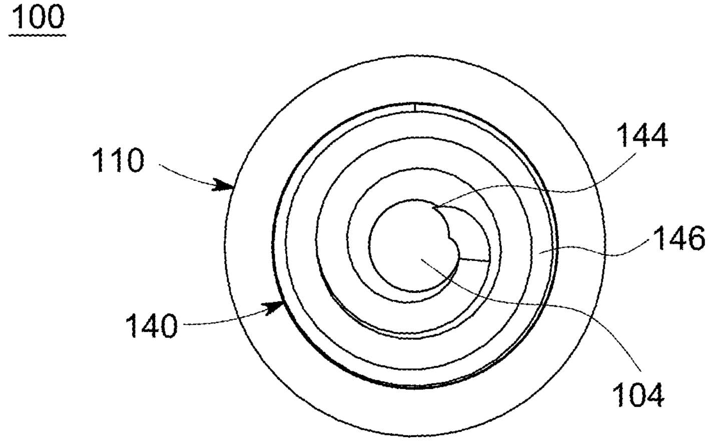
FIG. 8 is a bottom view of the implantable screw of FIG. 1, in accordance with an aspect of the present disclosure.
Figure 9:
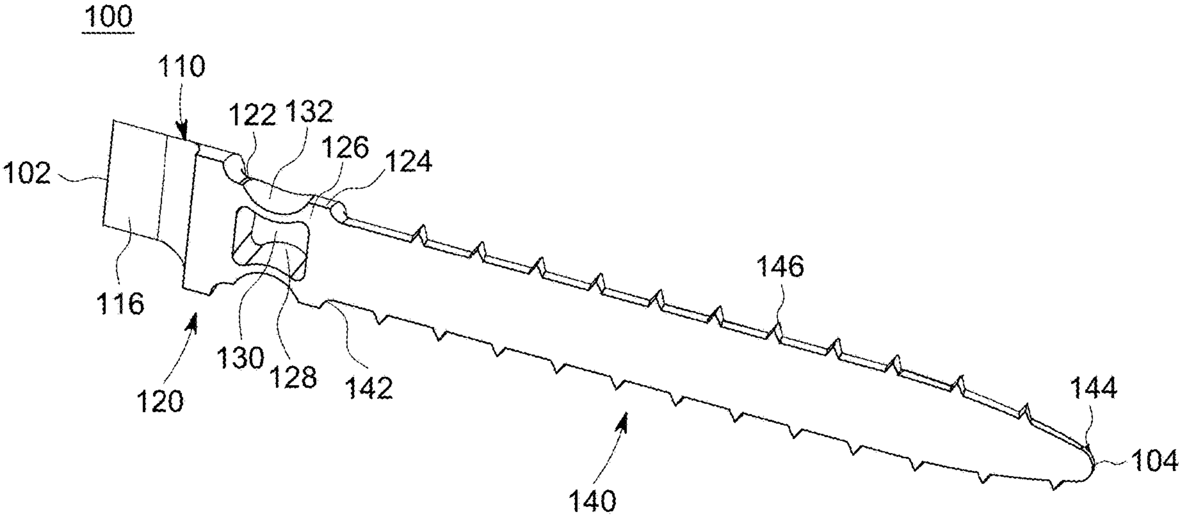
FIG. 9 is a first perspective, cross-sectional view of the implantable screw of FIG. 1 taken along line 9-9 in FIG. 7, in accordance with an aspect of the present disclosure.
Figure 10:
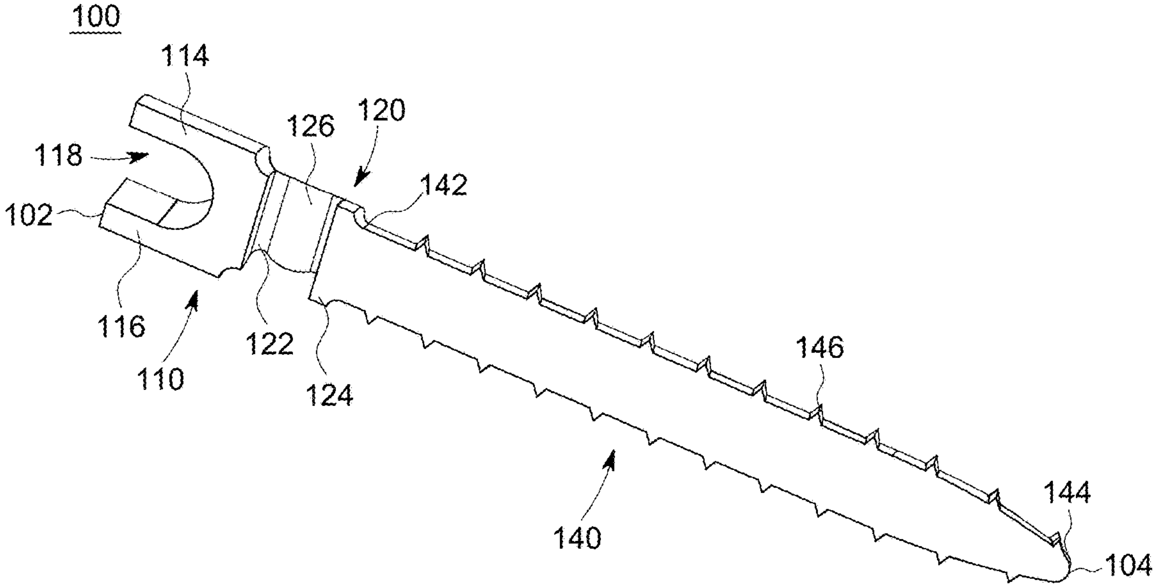
FIG. 10 is a second perspective, cross-sectional view of the implantable screw of FIG. 1 taken along line 10-10 in FIG. 7, in accordance with an aspect of the present disclosure.
Figure 11:
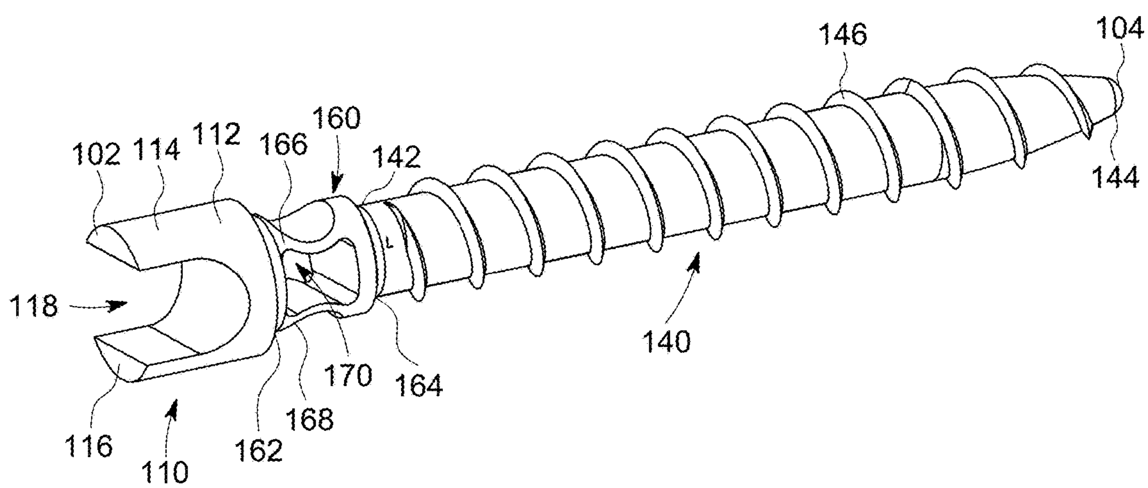
FIG. 11 is a first perspective view of another implantable screw, in accordance with an aspect of the present disclosure.
Figure 12:
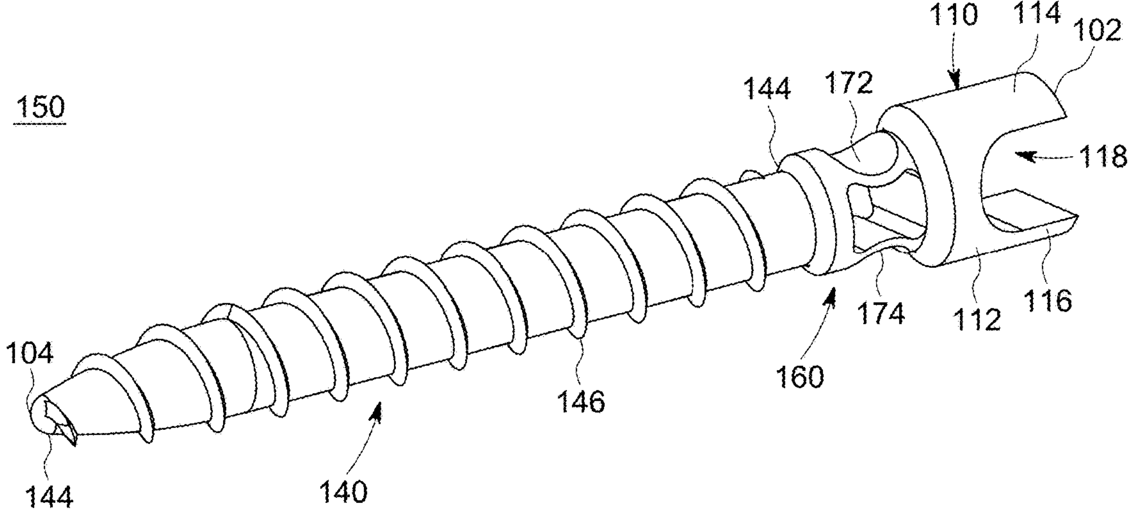
FIG. 12 is a second perspective view of the implantable screw of FIG. 11, in accordance with an aspect of the present disclosure.
Figure 13:
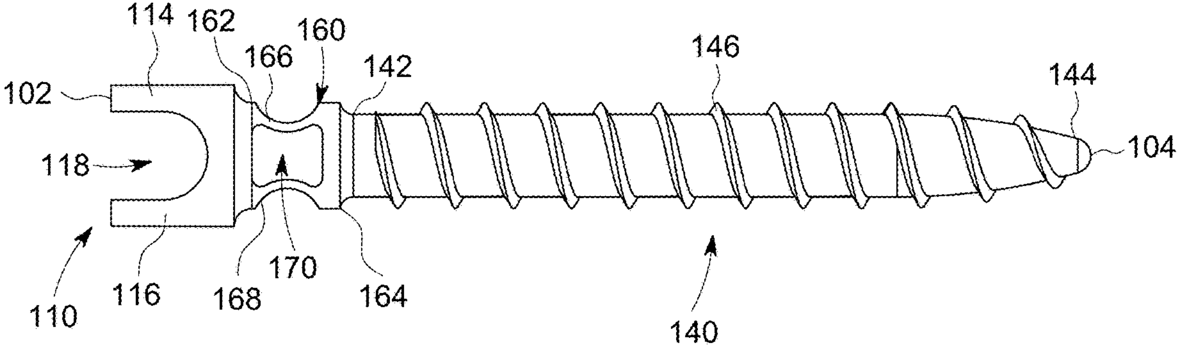
FIG. 13 is a first side view of the implantable screw of FIG. 11, in accordance with an aspect of the present disclosure.
Figure 14:
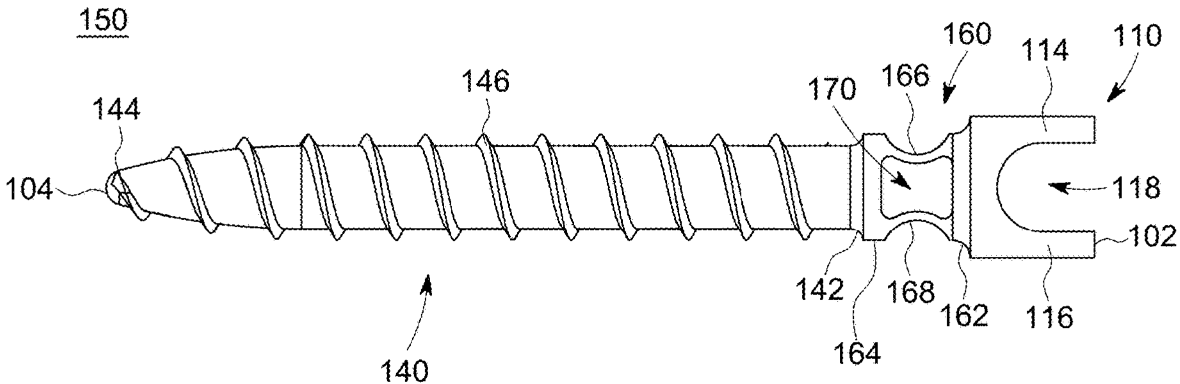
FIG. 14 is a second side view of the implantable screw of FIG. 11, in accordance with an aspect of the present disclosure.
Figure 15:
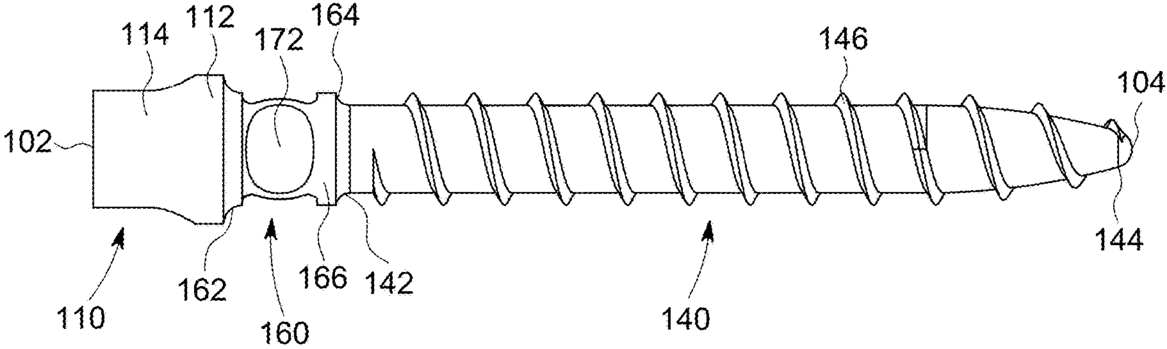
FIG. 15 is a first end view of the implantable screw of FIG. 11, in accordance with an aspect of the present disclosure.
Figure 16:
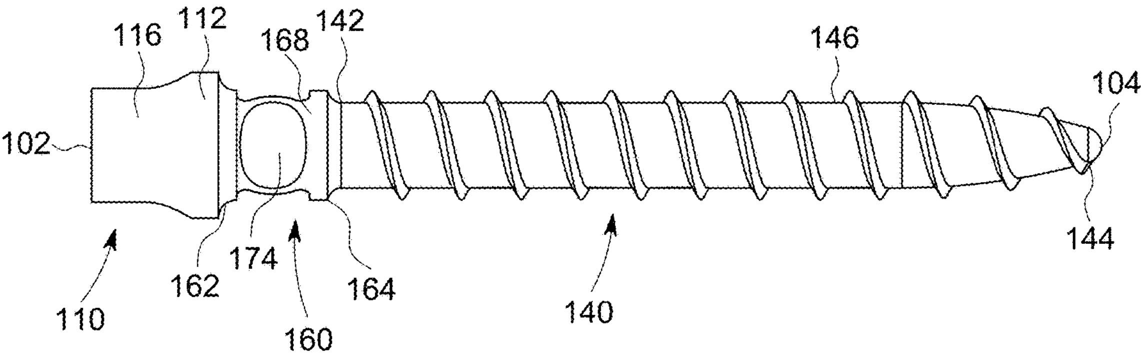
FIG. 16 is a second end view of the implantable screw of FIG. 11, in accordance with an aspect of the present disclosure.
Figure 17:
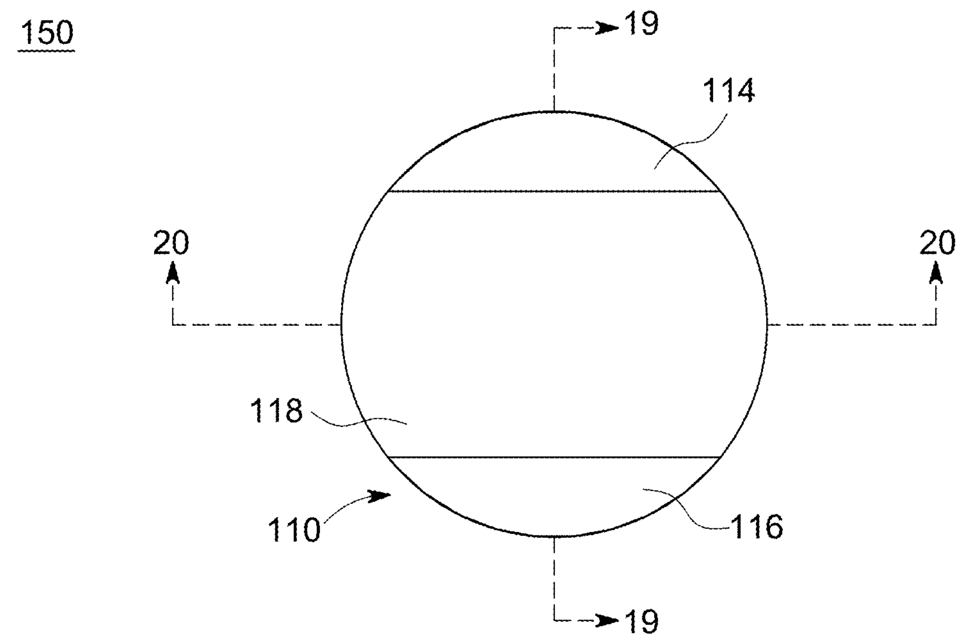
FIG. 17 is a top view of the implantable screw of FIG. 11, in accordance with an aspect of the present disclosure.
Figure 18:
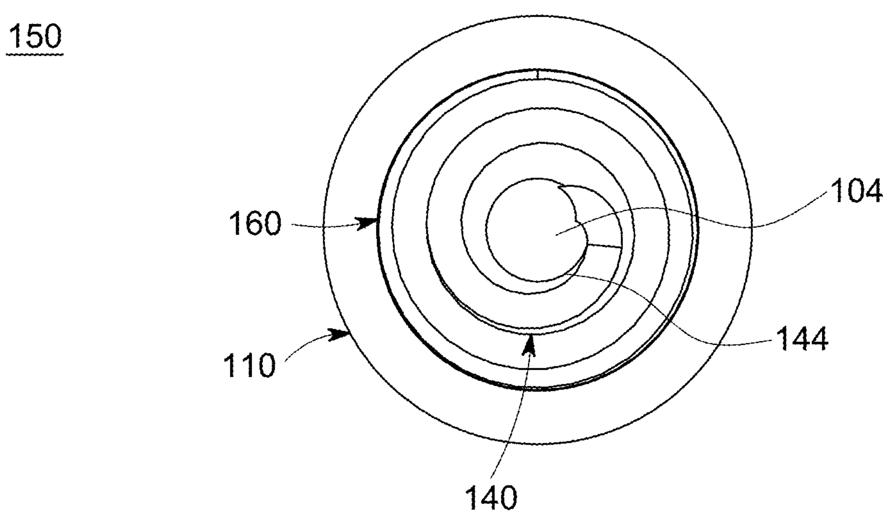
FIG. 18 is a bottom view of the implantable screw of FIG. 11, in accordance with an aspect of the present disclosure.
Figure 19:
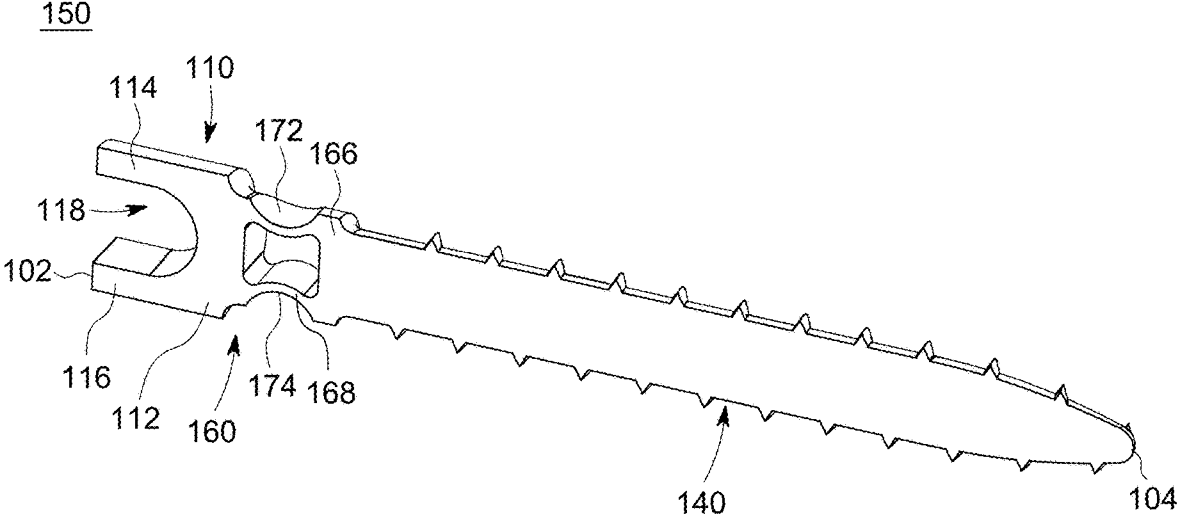
FIG. 19 is a first perspective, cross-sectional view of the implantable screw of FIG. 11 taken along line 19-19 of FIG. 17, in accordance with an aspect of the present disclosure.
Figure 20:
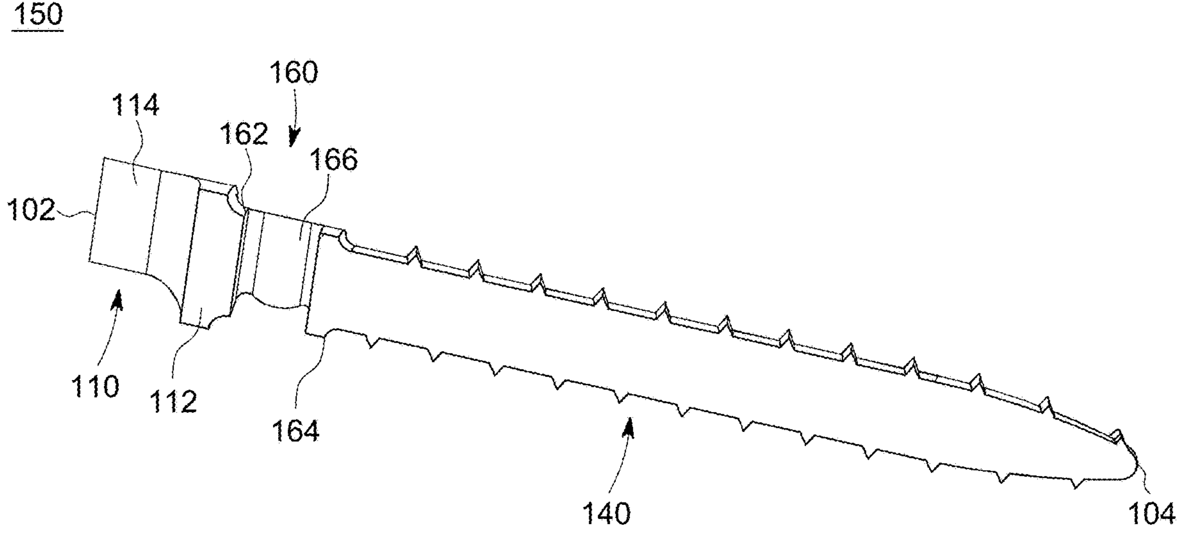
FIG. 20 is a second perspective, cross-sectional view of the implantable screw of FIG. 11 taken along line 20-20 in FIG. 17, in accordance with an aspect of the present disclosure.
Figure 21:
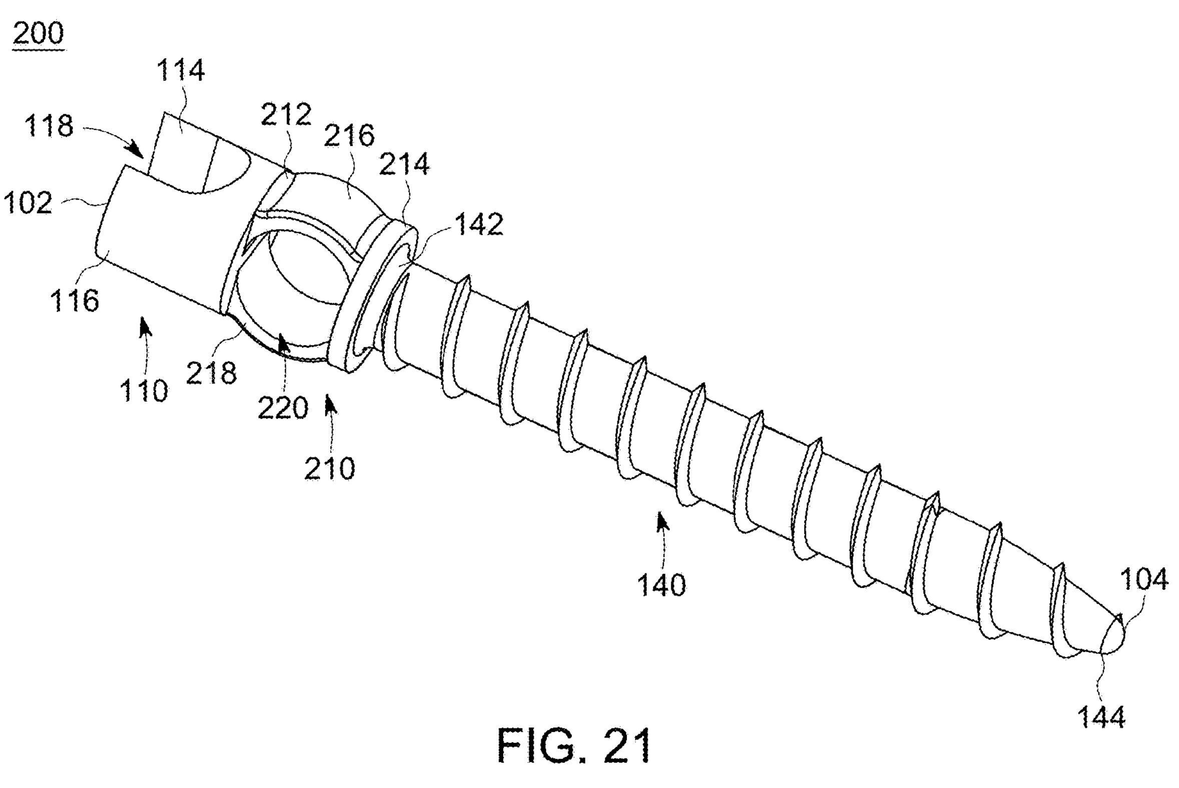
FIG. 21 is a first perspective view of another implantable screw, in accordance with an aspect of the present disclosure.
Figure 22:
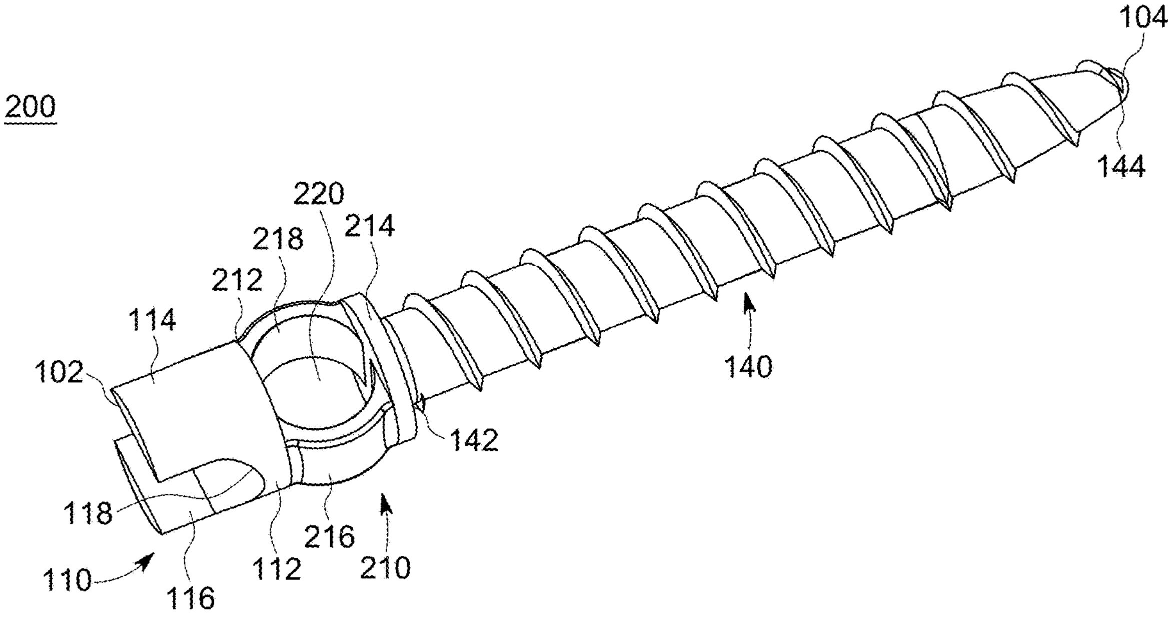
FIG. 22 is a second perspective view of the implantable screw of FIG. 21, in accordance with an aspect of the present disclosure.
Figure 23:
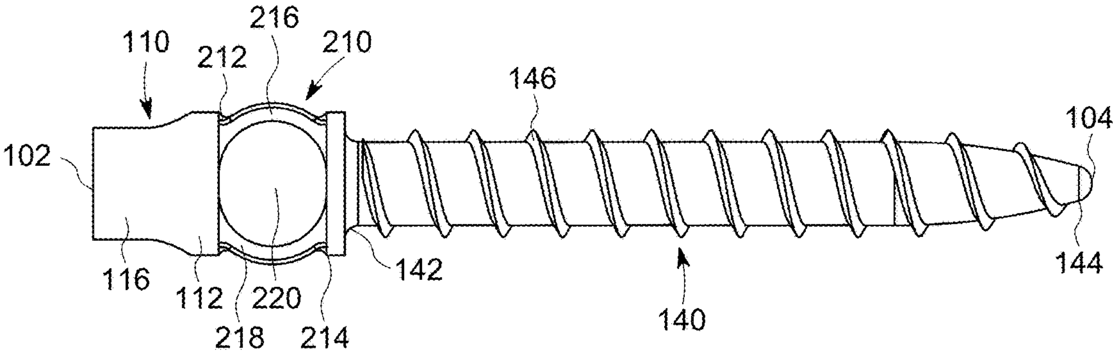
FIG. 23 is a first side view of the implantable screw of FIG. 21, in accordance with an aspect of the present disclosure.
Figure 24:
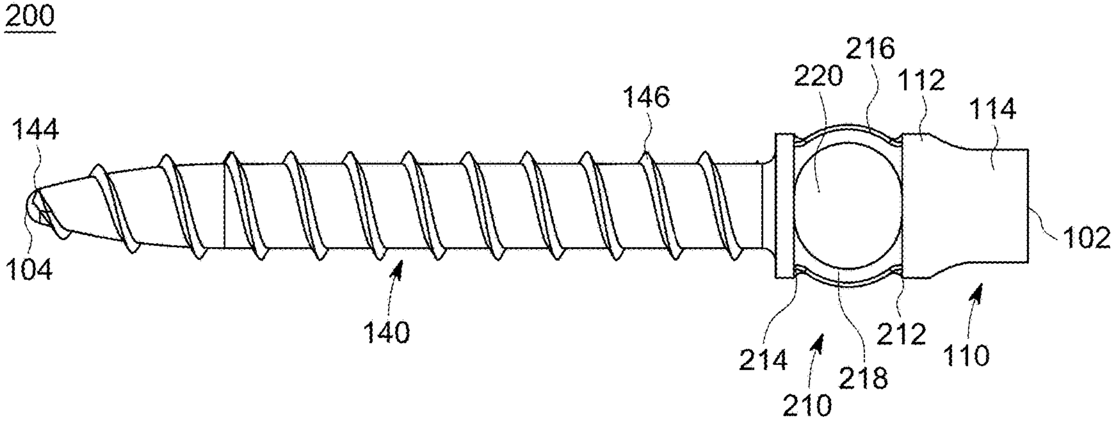
FIG. 24 is a second side view of the implantable screw of FIG. 21, in accordance with an aspect of the present disclosure.
Figure 25:
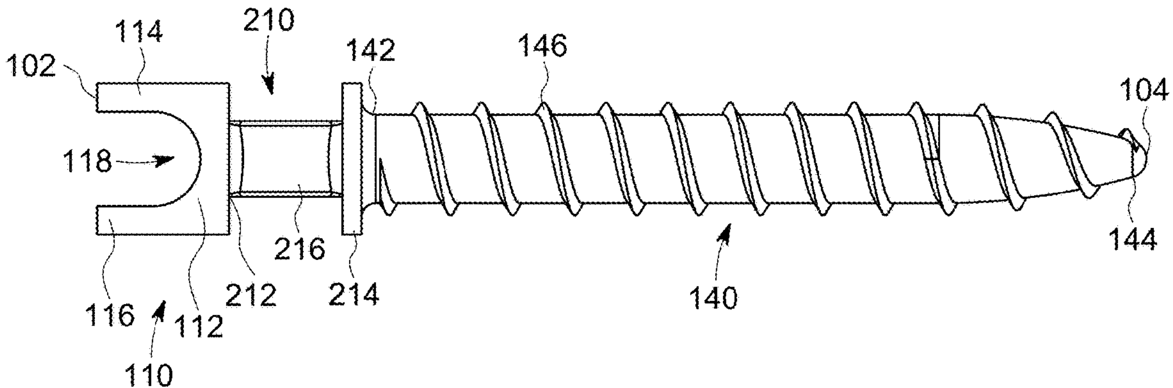
FIG. 25 is a first end view of the implantable screw of FIG. 21, in accordance with an aspect of the present disclosure.
Figure 26:
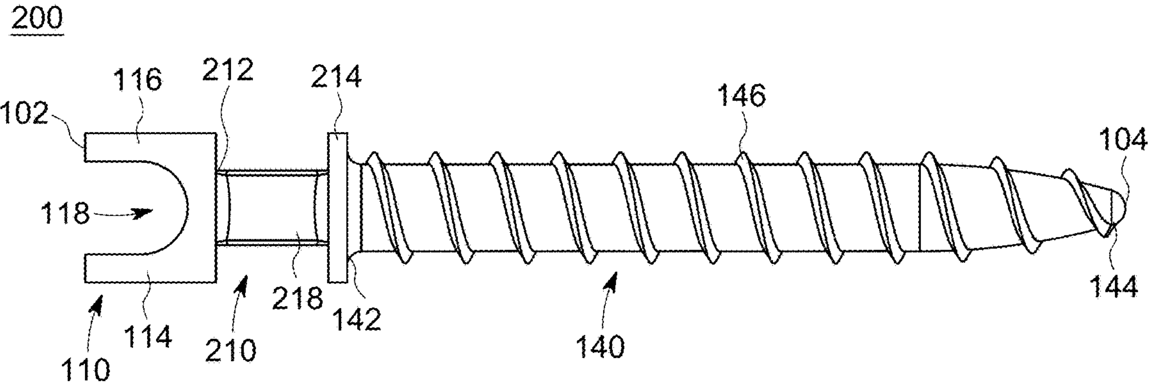
FIG. 26 is a second end view of the implantable screw of FIG. 21, in accordance with an aspect of the present disclosure.
Figure 27:
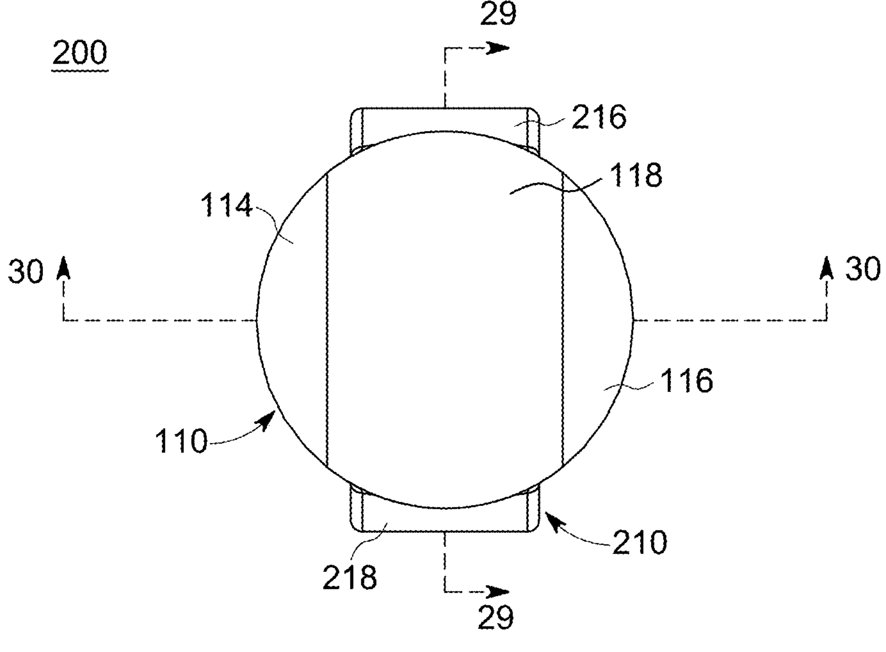
FIG. 27 is a top view of the implantable screw of FIG. 21, in accordance with an aspect of the present disclosure.
Figure 28:
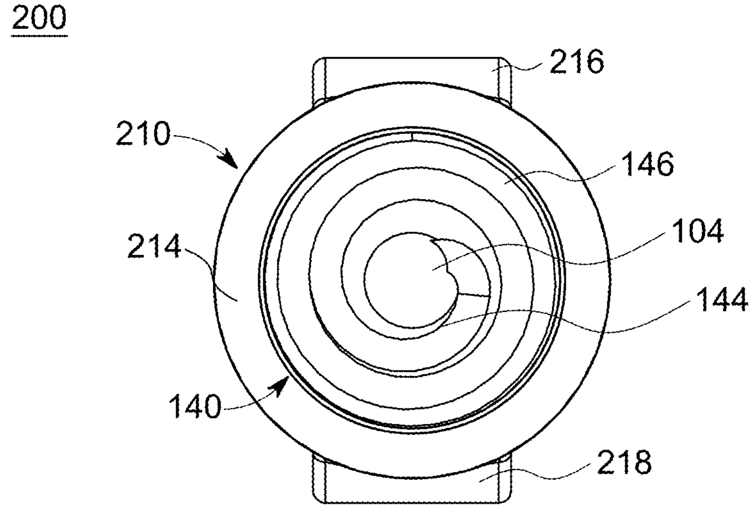
FIG. 28 is a bottom view of the implantable screw of FIG. 21, in accordance with an aspect of the present disclosure.
Figures 29, 30:
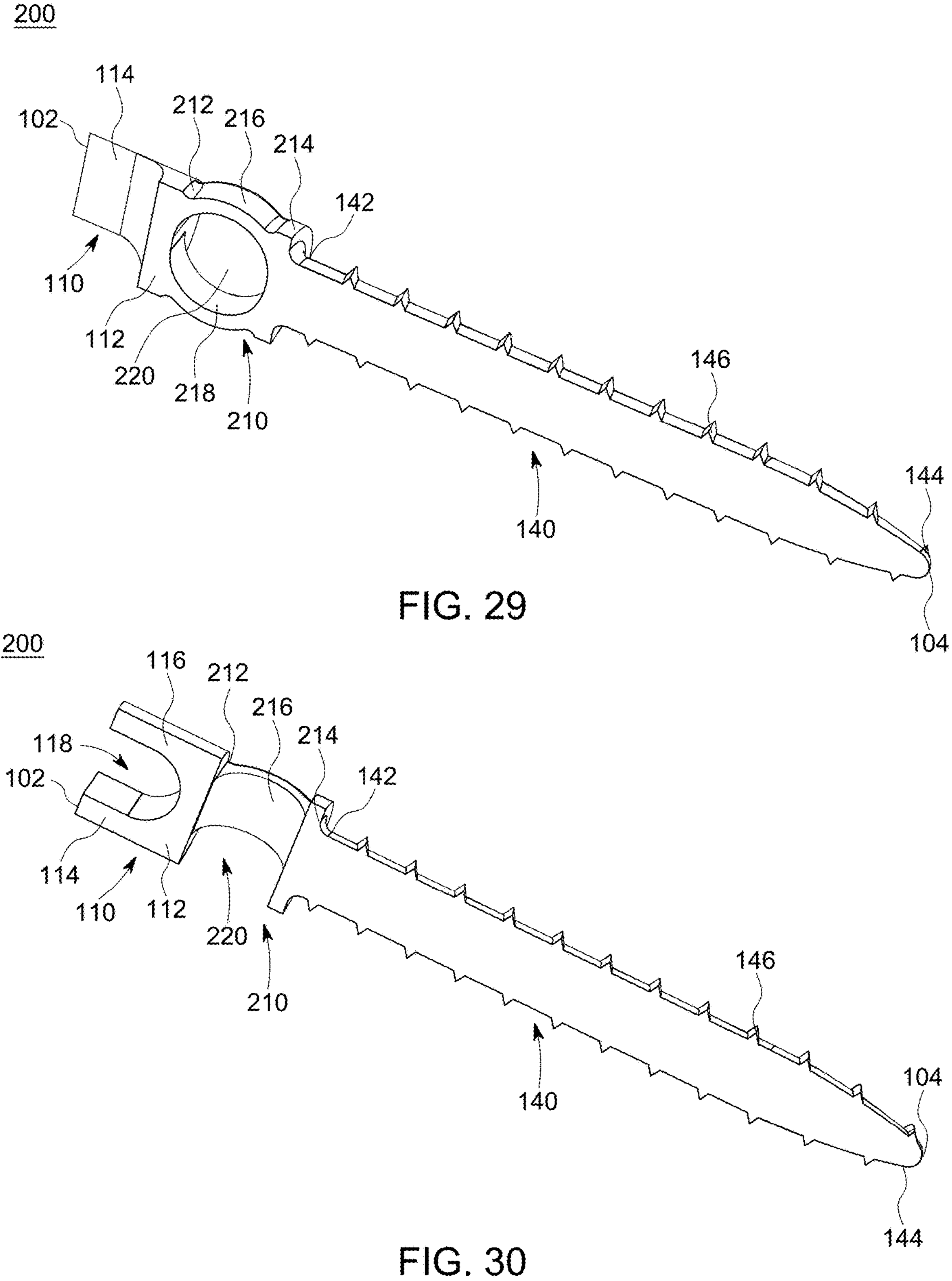
FIG. 29 is a first perspective, cross-sectional view of the implantable screw of FIG. 21 taken along line 29-29 in FIG. 27, in accordance with an aspect of the present disclosure.
FIG. 30 is a second perspective, cross-sectional view of the implantable screw of FIG. 21 taken along line 30-30 in FIG. 27, in accordance with an aspect of the present disclosure.
Figures 31, 32:
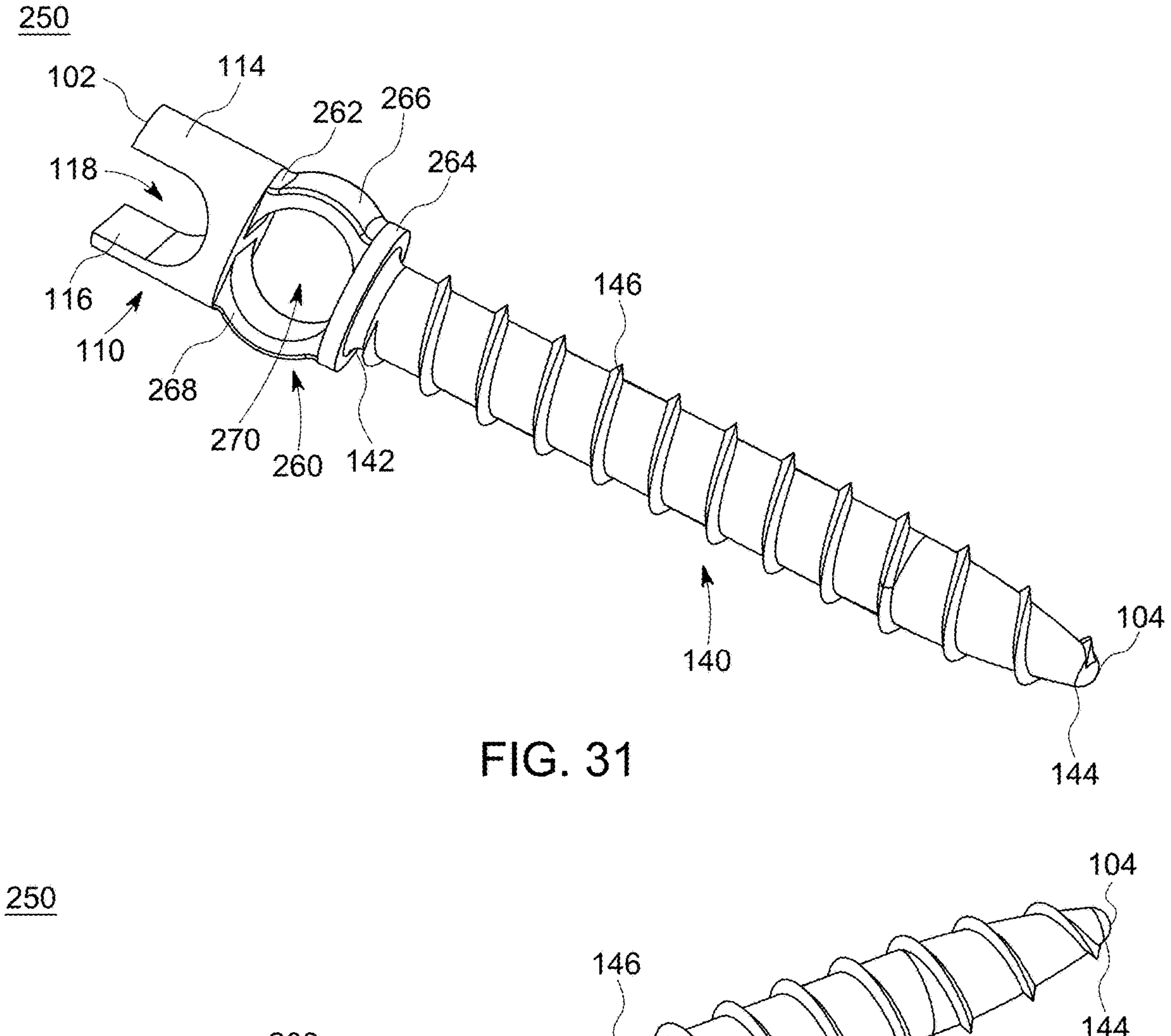
FIG. 31 is a first perspective view of another implantable screw, in accordance with an aspect of the present disclosure.
FIG. 32 is a second perspective view of the implantable screw of FIG. 31, in accordance with an aspect of the present disclosure.
Figure 33:
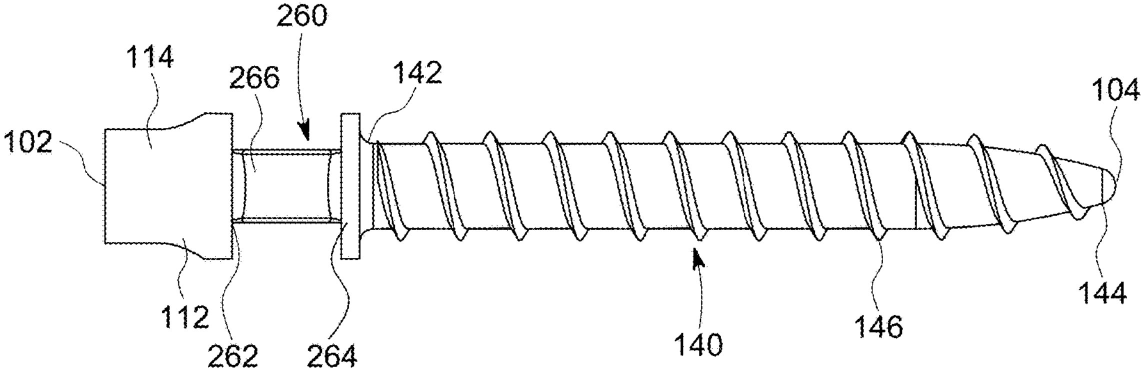
FIG. 33 is a first side view of the implantable screw of FIG. 31, in accordance with an aspect of the present disclosure.
Figure 34:
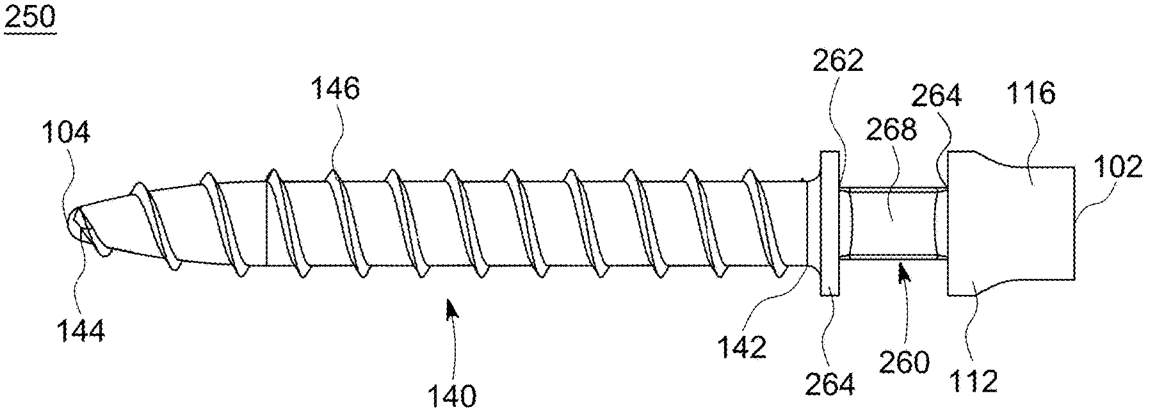
FIG. 34 is a second side view of the implantable screw of FIG. 31, in accordance with an aspect of the present disclosure.
Figure 35:
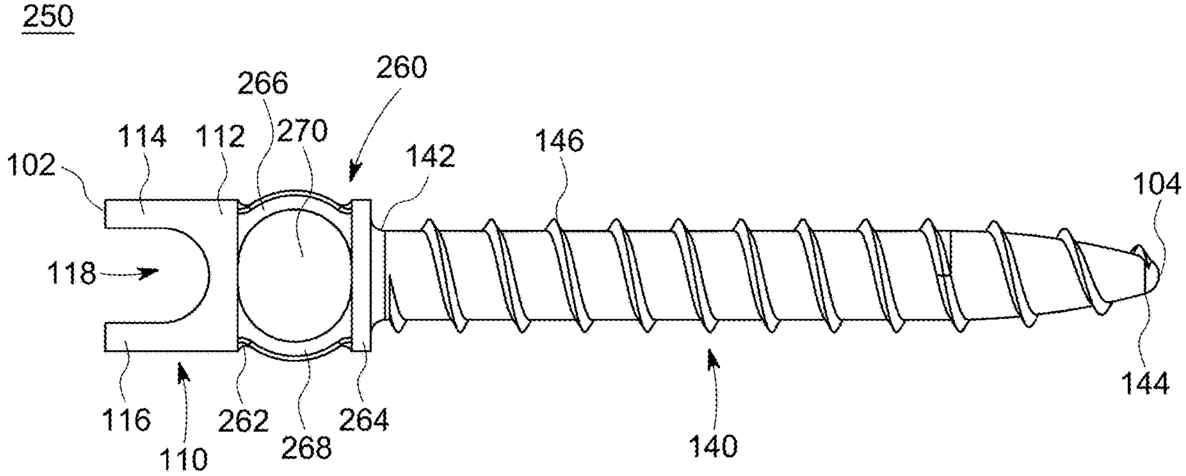
FIG. 35 is a first end view of the implantable screw of FIG. 31, in accordance with an aspect of the present disclosure.
Figure 36:
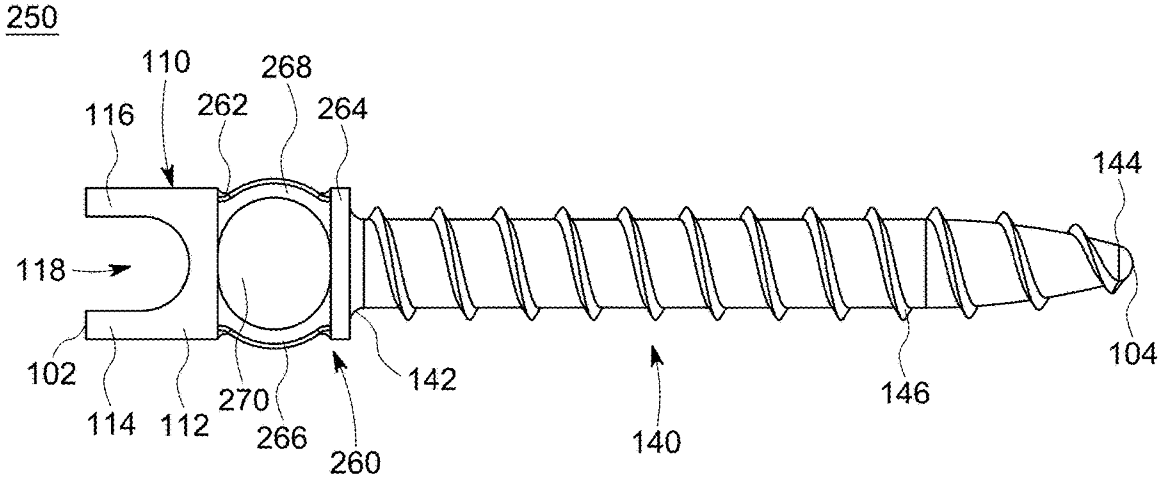
FIG. 36 is a second end view of the implantable screw of FIG. 31, in accordance with an aspect of the present disclosure.
Figure 37:
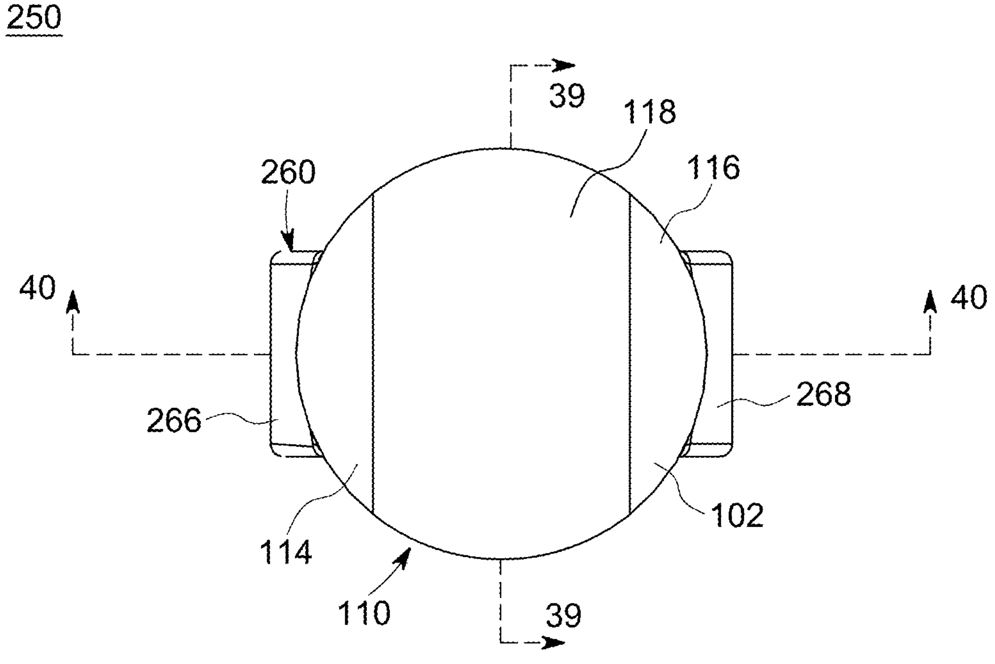
FIG. 37 is a top view of the implantable screw of FIG. 31, in accordance with an aspect of the present disclosure.
Figure 38:
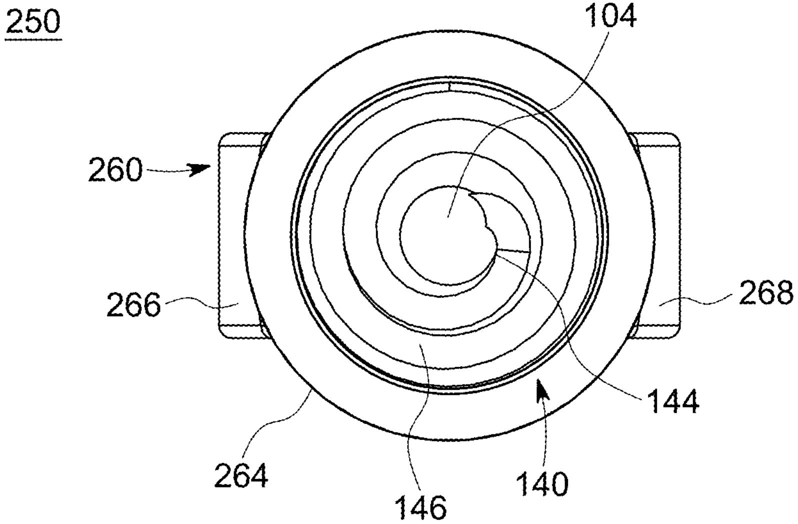
FIG. 38 is a bottom view of the implantable screw of FIG. 31, in accordance with an aspect of the present disclosure.
Figures 39, 40:
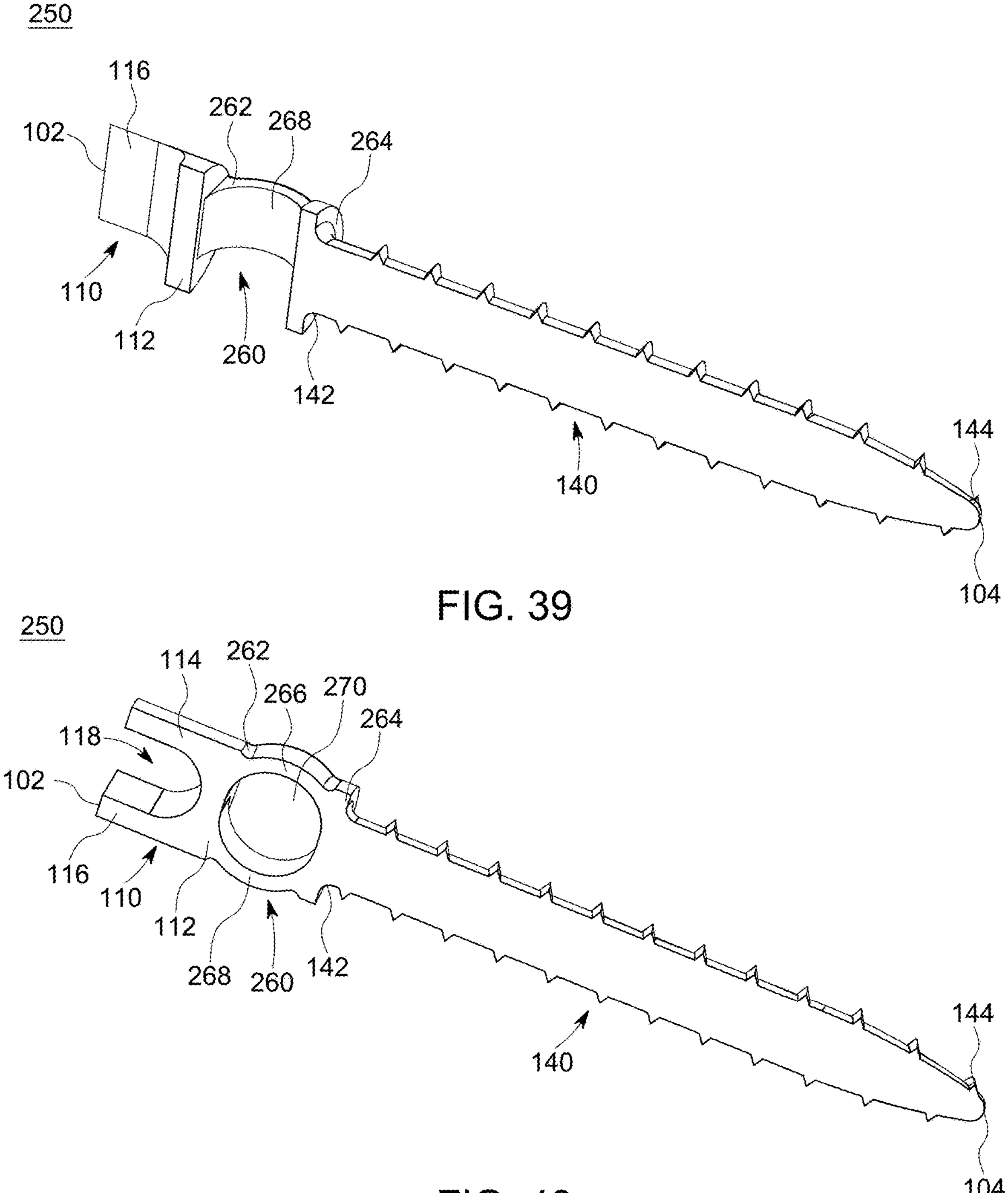
FIG. 39 is a first perspective, cross-sectional view of the implantable screw of FIG. 11 taken along line 39-39 of FIG. 37, in accordance with an aspect of the present disclosure.
FIG. 40 is a second perspective, cross-sectional view of the implantable screw of FIG. 31 taken along line 40-40 in FIG. 37, in accordance with an aspect of the present disclosure.
Figure 41:
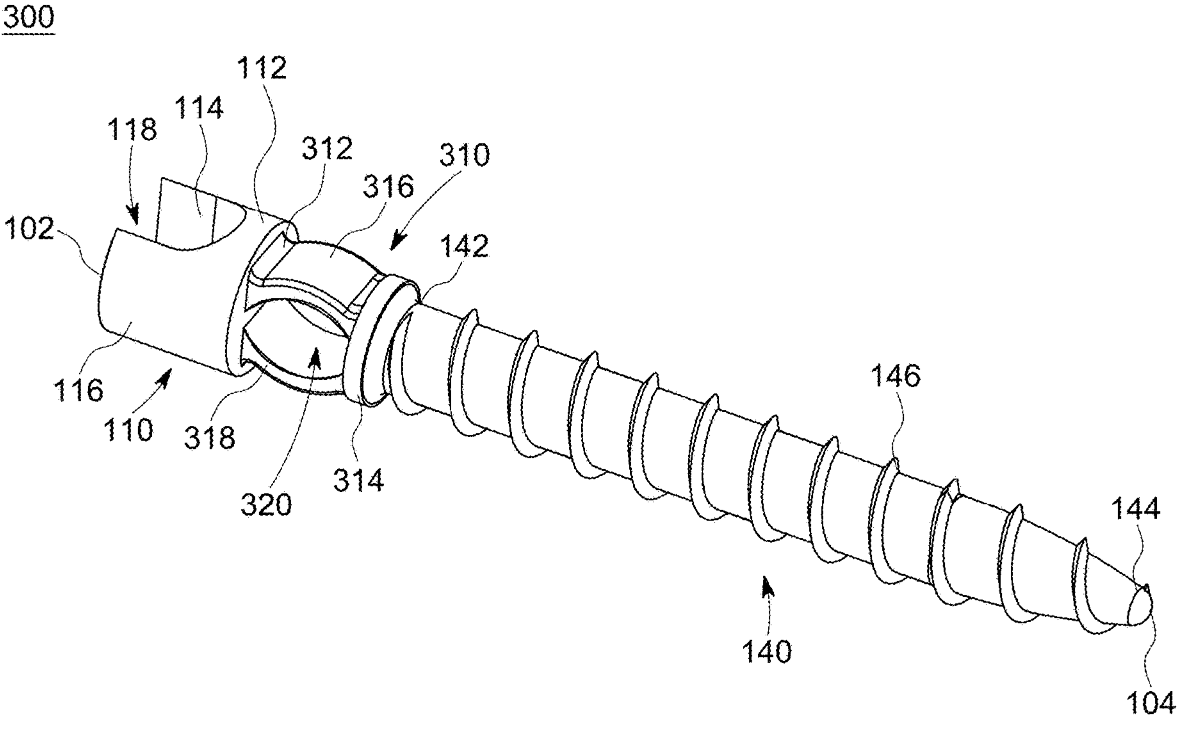
FIG. 41 is a first perspective view of another implantable screw, in accordance with an aspect of the present disclosure.
Figure 42:
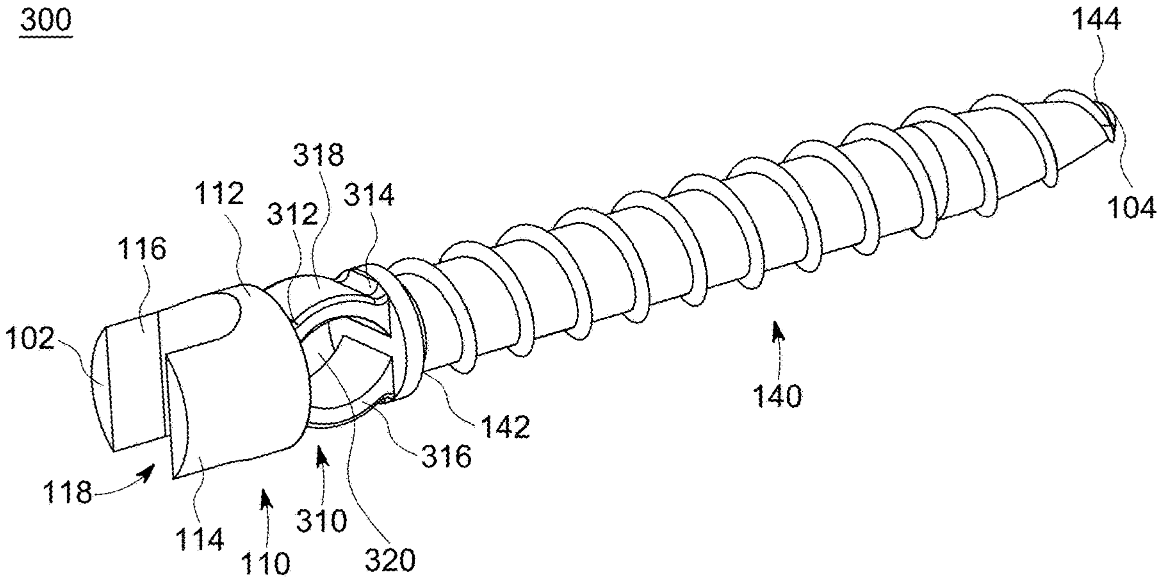
FIG. 42 is a second perspective view of the implantable screw of FIG. 41, in accordance with an aspect of the present disclosure.
Figure 43:
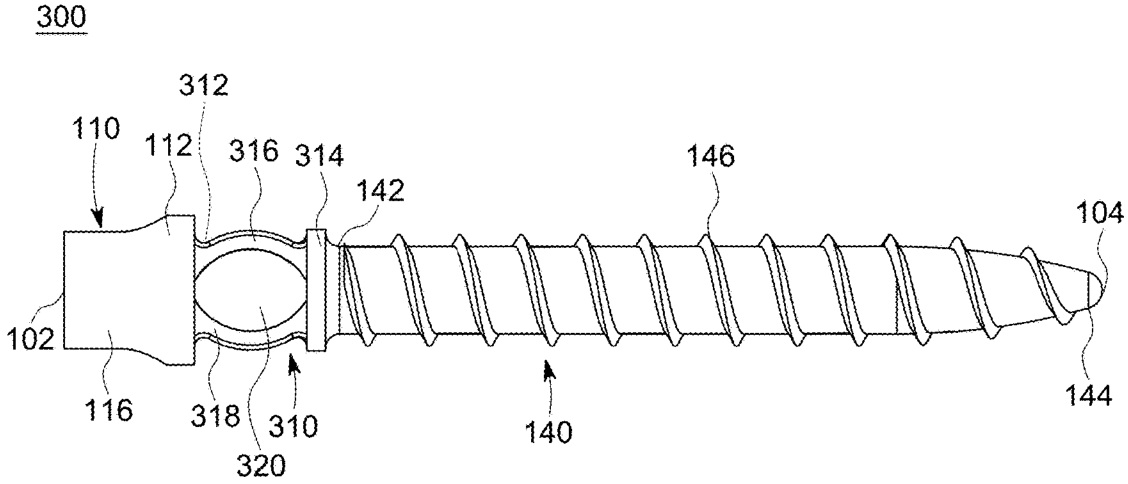
FIG. 43 is a first side view of the implantable screw of FIG. 41, in accordance with an aspect of the present disclosure.
Figure 44:
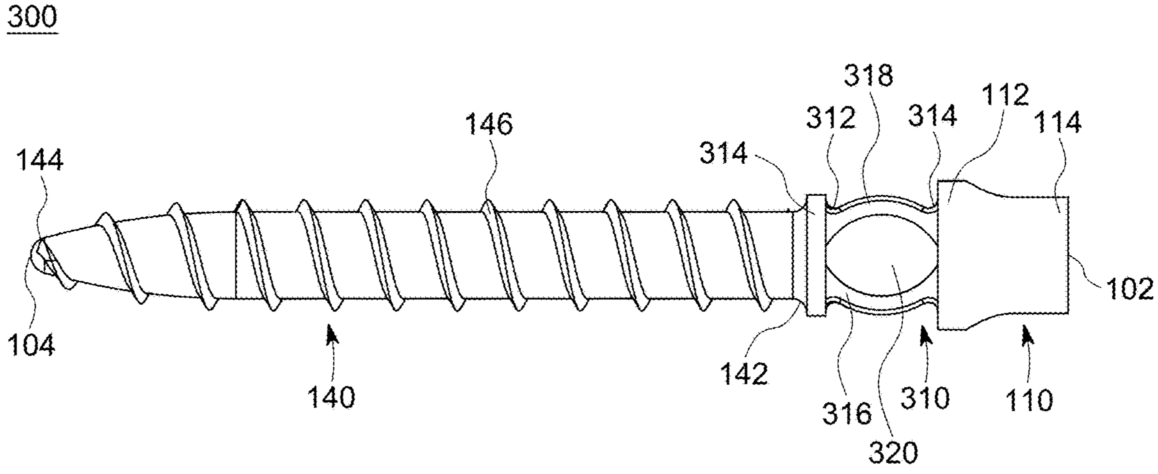
FIG. 44 is a second side view of the implantable screw of FIG. 41, in accordance with an aspect of the present disclosure.
Figure 45:
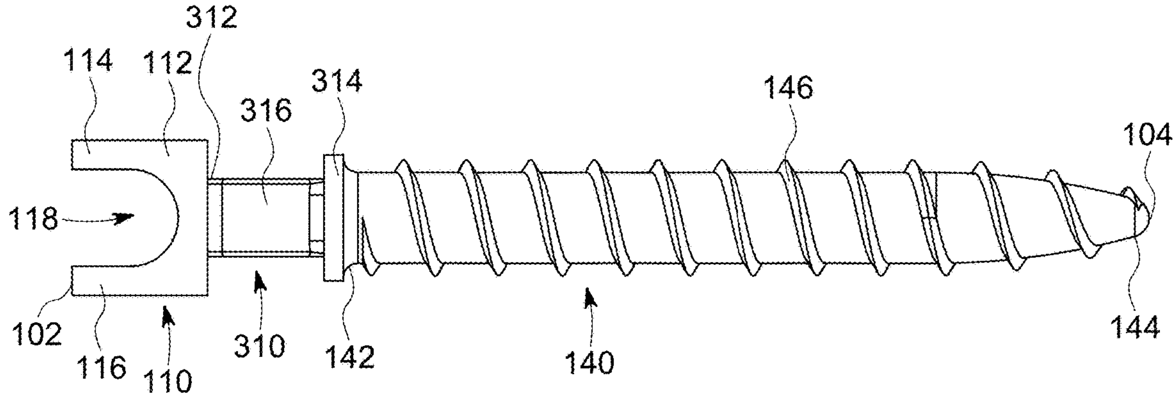
FIG. 45 is a first end view of the implantable screw of FIG. 41, in accordance with an aspect of the present disclosure.
Figure 46:
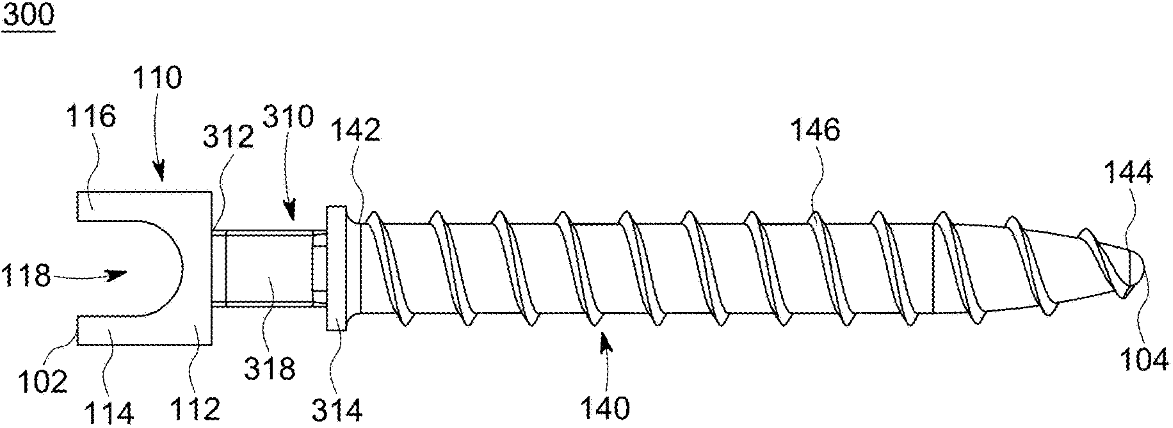
FIG. 46 is a second end view of the implantable screw of FIG. 41, in accordance with an aspect of the present disclosure.
Figure 47:
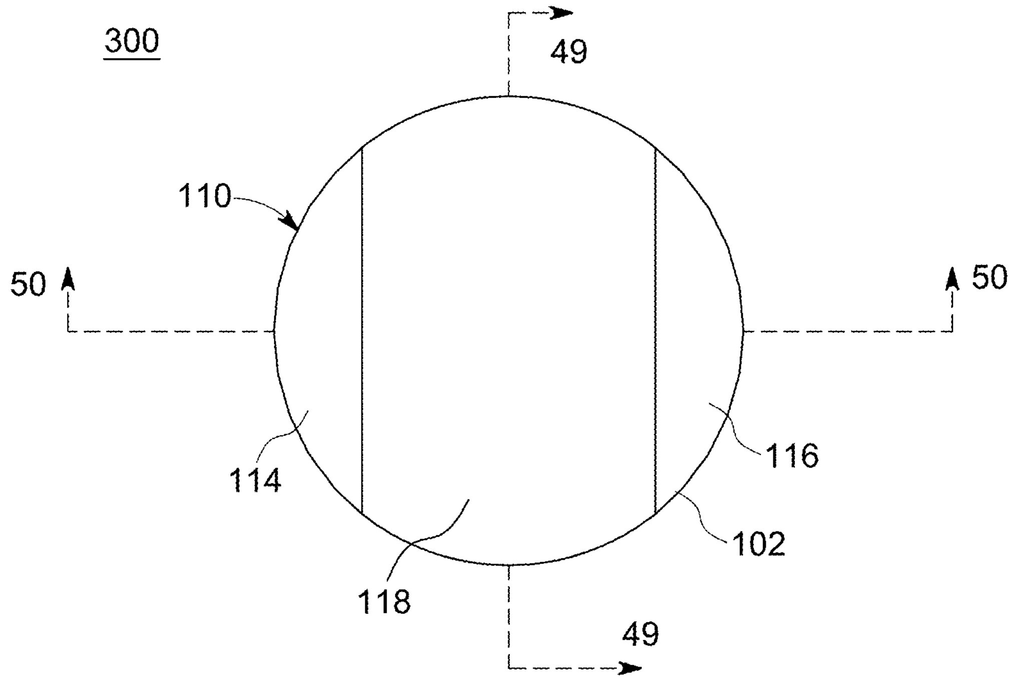
FIG. 47 is a top view of the implantable screw of FIG. 41, in accordance with an aspect of the present disclosure.
Figure 48:
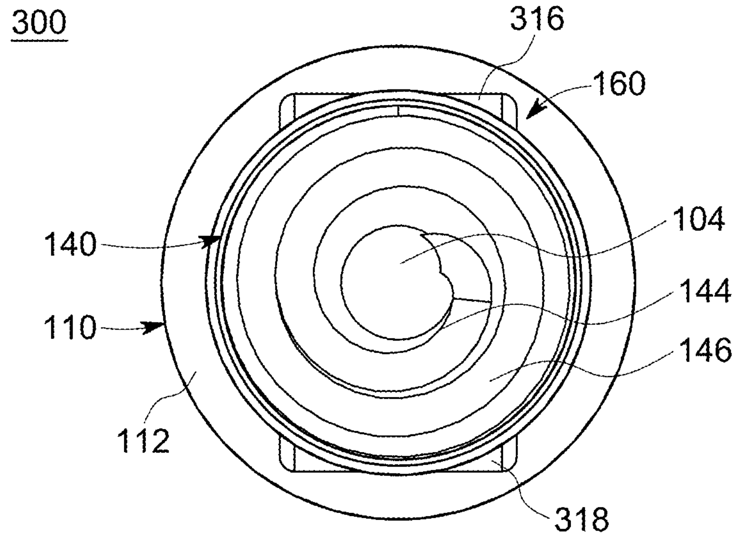
FIG. 48 is a bottom view of the implantable screw of FIG. 41, in accordance with an aspect of the present disclosure.
Figures 49, 50:
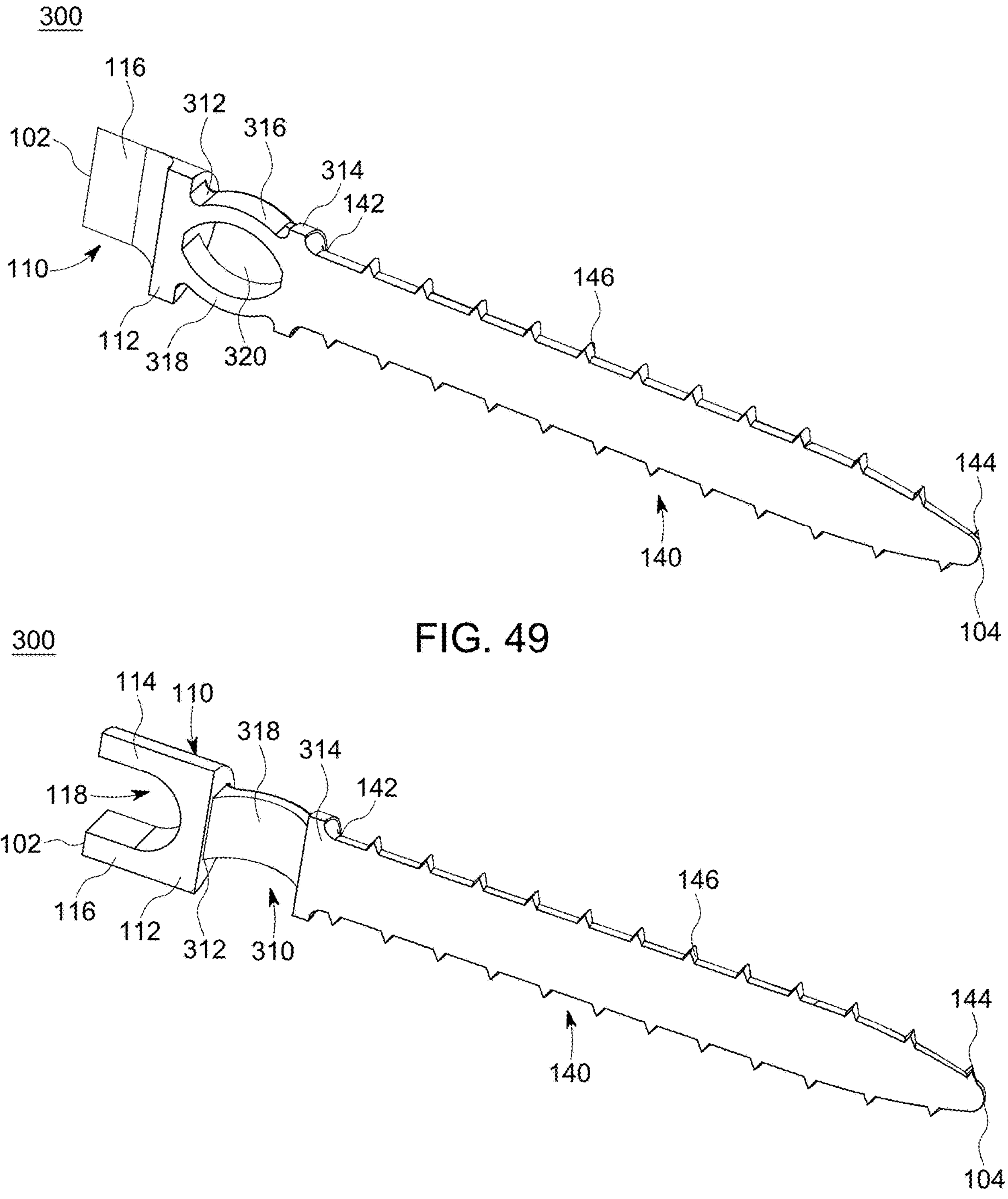
FIG. 49 is a first perspective, cross-sectional view of the implantable screw of FIG. 41 taken along line 49-49 of FIG. 47, in accordance with an aspect of the present disclosure.
FIG. 50 is a second perspective, cross-sectional view of the implantable screw of FIG. 41 taken along line 40-40 in FIG. 47, in accordance with an aspect of the present disclosure.
Figures 51, 52:
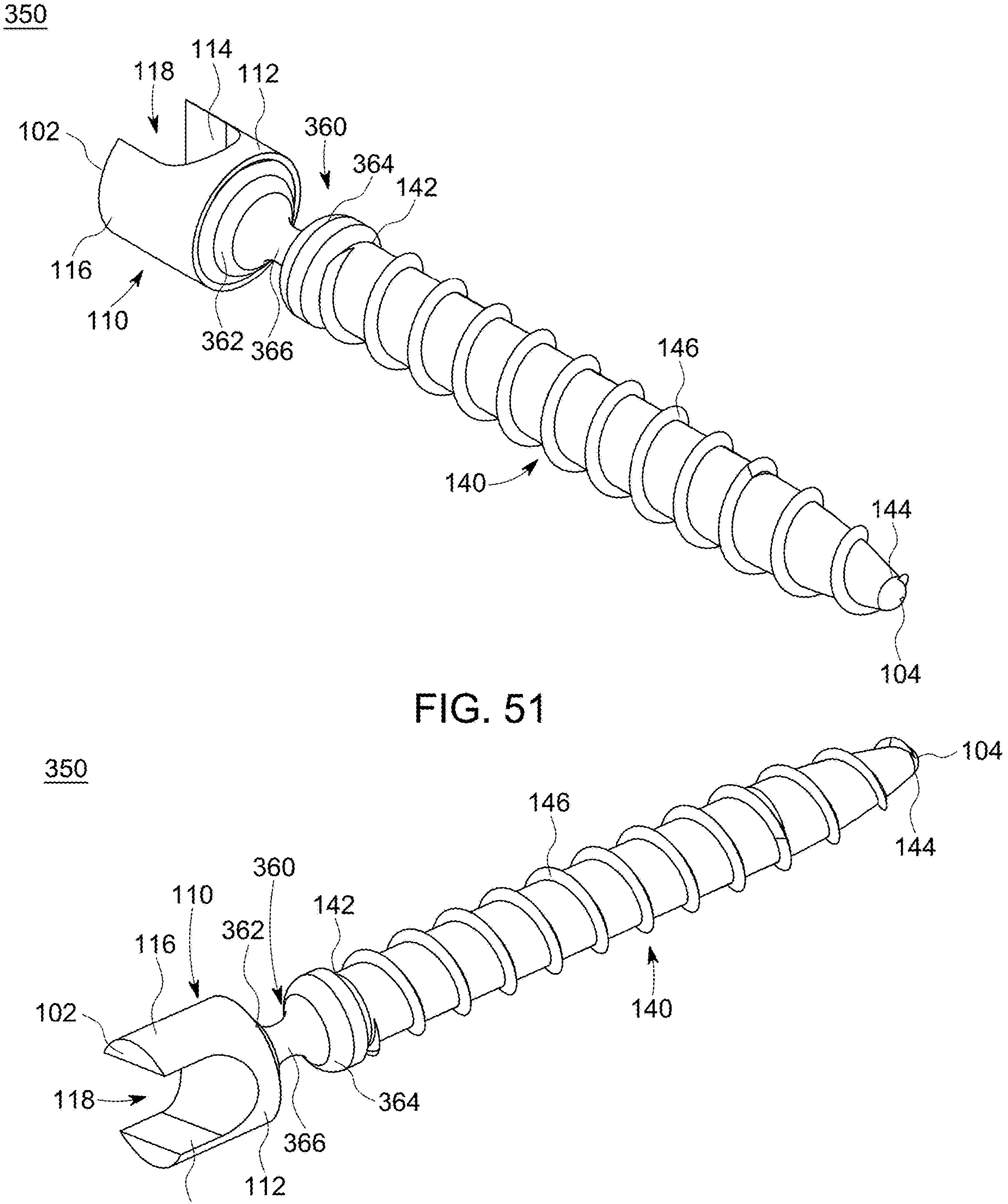
FIG. 51 is a first perspective view of another implantable screw, in accordance with an aspect of the present disclosure.
FIG. 52 is a second perspective view of the implantable screw of FIG. 51, in accordance with an aspect of the present disclosure.
Figure 53:
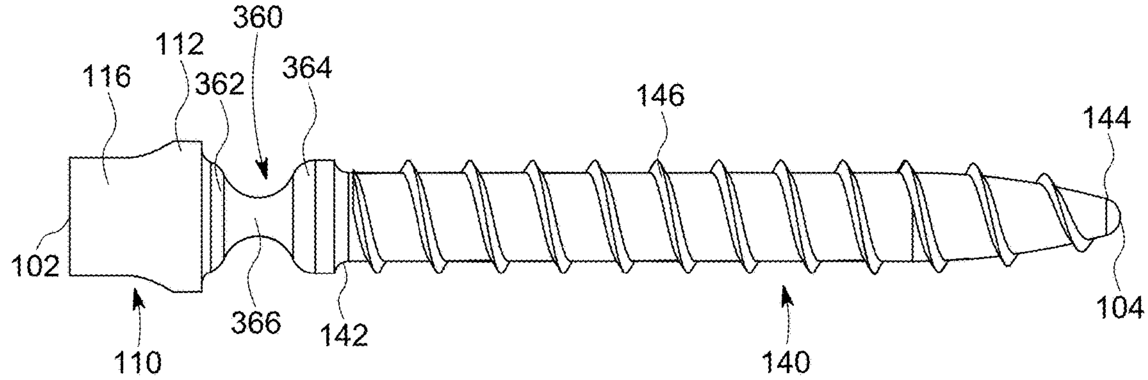
FIG. 53 is a side view of the implantable screw of FIG. 51, in accordance with an aspect of the present disclosure.
Figure 54:
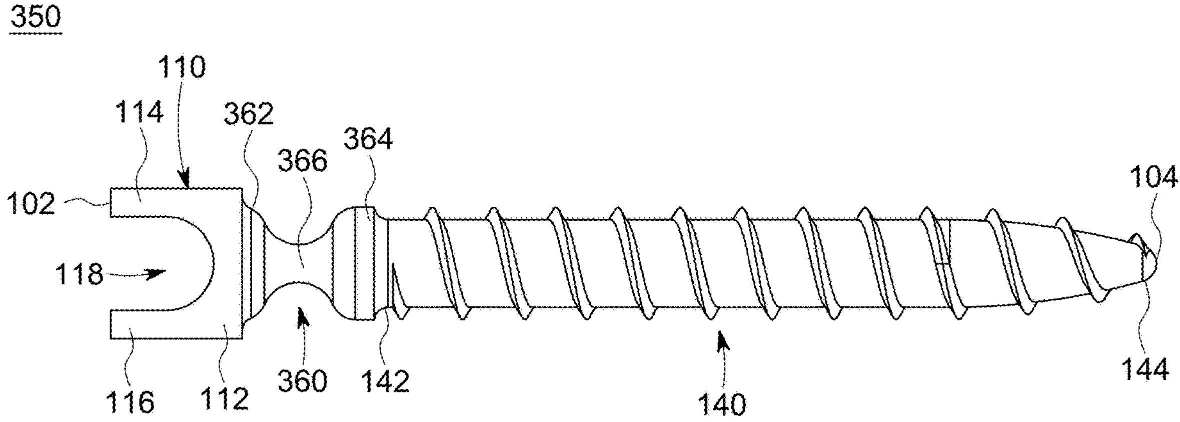
FIG. 54 is an end view of the implantable screw of FIG. 51, in accordance with an aspect of the present disclosure.
Figure 55:
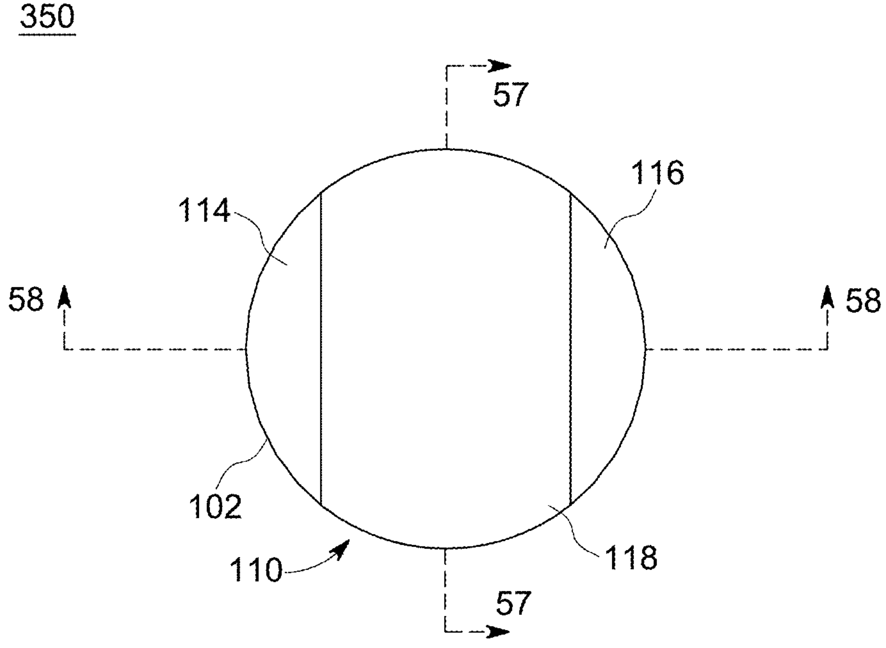
FIG. 55 is a top view of the implantable screw of FIG. 51, in accordance with an aspect of the present disclosure.
Figure 56:
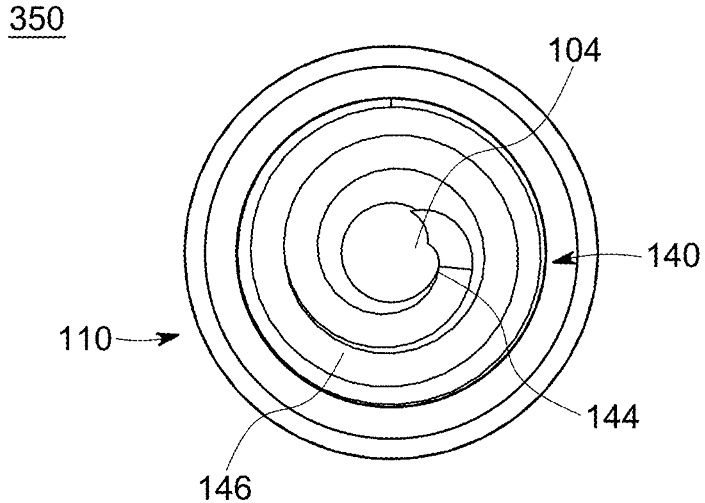
FIG. 56 is a bottom view of the implantable screw of FIG. 51, in accordance with an aspect of the present disclosure.
Figure 57:
FIG. 57 is a first perspective, cross-sectional view of the implantable screw of FIG. 51 taken along line 57-57 in FIG. 55, in accordance with an aspect of the present disclosure.
Figure 57:
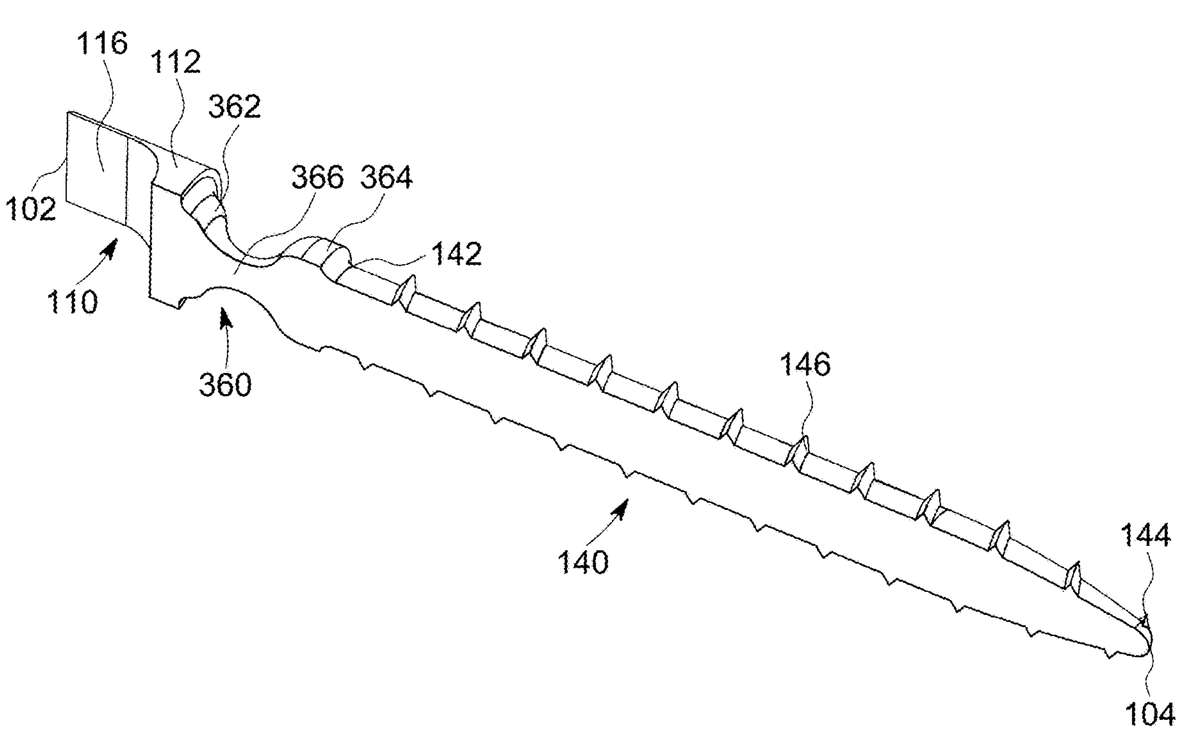
Figure 58:
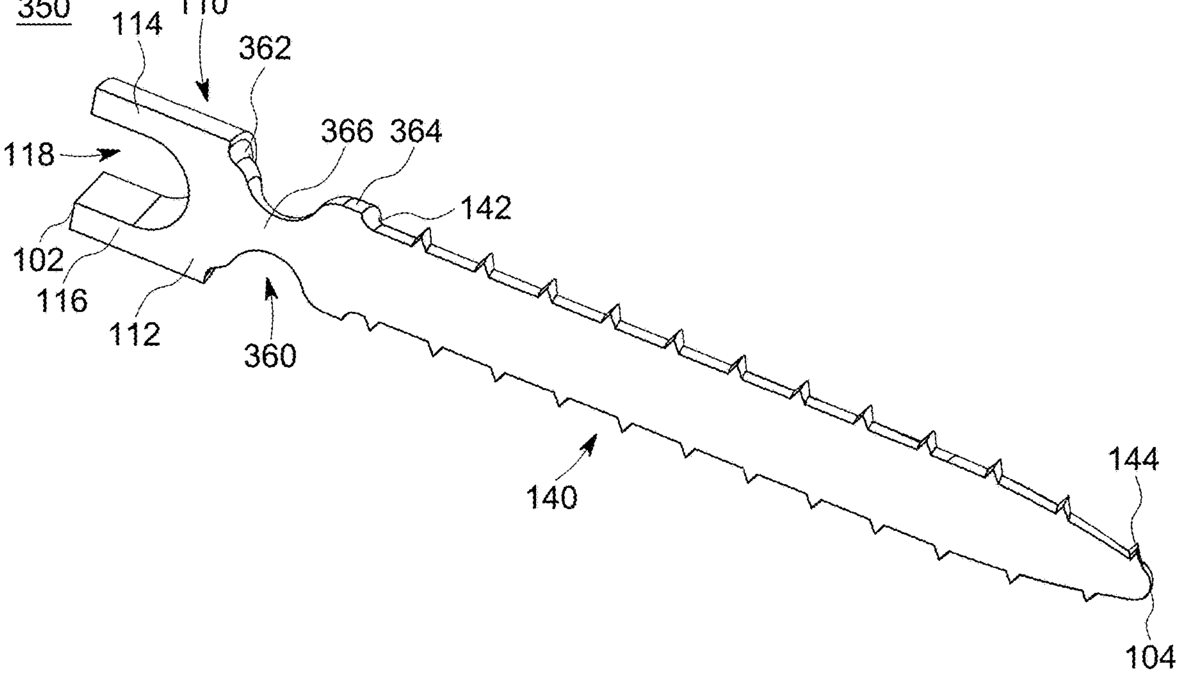
FIG. 58 is a second perspective, cross-sectional view of the implantable screw of FIG. 31 taken along line 58-58 in FIG. 55, in accordance with an aspect of the present disclosure.

Referring to the drawings, wherein like reference numerals are used to indicate like or analogous components throughout the several views, and with particular reference to FIGS. 1-58 implantable screws 100, 150, 200, 250, 300, 350 are shown. The screws 100, 150, 200, 250, 300, 350 may be, for example, implanted into at least one bone or bone fragment. The screws 100, 150, 200, 250, 300, 350 may be, for example, pedicle screws for insertion into the vertebrae of the spine.

With reference to FIGS. 1-58, implants or implantable screws 100, 150, 200, 250, 300, 350 are shown. The screws 100, 150, 200, 250, 300, 350 have a first or proximal end 102 and a second or distal end 104. The screws 100, 150, 200, 250, 300, 350 includes head portions, proximal sections, or tulips 110, middle sections or portions 120, 160, 210, 260, 310, 360, and shafts, distal sections, or threaded shafts 140. The middle sections 120, 160, 210, 260, 310, 360 couple the head portions 110 to the shafts 140. The head portions 110 may be used to drive the screws 100, 150, 200, 250, 300, 350 into the at least one bone or bone fragment. The head portions 110 may also be dimensioned and configured to receive a driver or other tool for driving the screws 100, 150, 200, 250, 300, 350 into the at least one bone or bone fragment. The middle sections 120, 160, 210, 260, 310, 360 may be, for example, short or long. The middle sections 120, 160, 210, 260, 310, 360 may have a length of, for example, approximately 1 mm to approximately 10 mm, more preferably approximately 3.5 mm to approximately 7.5 mm. The shafts 140 are configured for engagement in at least one bone or bone fragment.

The screws 100, 150, 200, 250, 300, 350 may be, for example, monolithic or a single piece of material. The screws 100, 150, 200, 250, 300, 350 may be made from, for example, titanium, a titanium alloy, stainless steel, a stainless steel alloy, ceramic, such as alumina, silicon nitride, carbon black, titanium dioxide, bioactive glass, or other biocompatible ceramic, or a biocompatible polymer, polymer blend, or a composite that is a combination of other biocompatible materials. In another embodiment, the screws 100, 150, 200, 250, 300, 350 may be, for example, multiple components assembled together. The head portions 110, middle portions 120, 160, 210, 260, 310, 360, and shafts 140 may be discrete components that are assembled or bonded together. The head portions 110, middle portions 120, 160, 210, 260, 310, 360, and shafts 140 may be bonded by, for example, welding, gluing, press-fitting, or other mechanical means of assembly.

The middle sections 120, 160, 210, 260, 310, 360 deform to allow some displacement or flex of the proximal sections 110 relative to the distal sections 140 under physiologic loading. The physiological loading may be, for example, flexion and/or extension. In an embodiment, when two implantable screws 100, 150, 200, 250, 300, 350 are connected to each other via at least one rod (not shown), the displacement or flex of the middle sections 120, 160, 210, 260, 310, 360 of at least one of the screws 100, 150, 200, 250, 300, 350 results in a deformation under physiologic loading of, for example, preferably between 0% and 20%, or more preferably between 2% to 10%, of the distance between the distal tips of the screws 100, 150, 200, 250, 300, 350. The deformation or flex of the proximal sections 110 relative to the distal sections 140 achieve this deformation or flex by straining of the middle sections 120, 160, 210, 260, 310, 360. The middle sections 120, 160, 210, 260, 310, 360 deform or strain only elastically under physiologic loading. The middle sections 120, 160, 210, 260, 310, 360 may also be made of, for example, a single element or multiple elements arranged in parallel or series. The middle sections 120, 160, 210, 260, 310, 360 allow for elastic deformation during physiologic loading.

With continued reference to FIGS. 1-58, each of the screws 100, 150, 200, 250, 300, 350 includes a head portion 110 and a shaft 140. The head portion 110 has a base 112 with two arms 114, 116 extending away from the base 112 toward the first end 102 of the screw 100. The first arm 114 extends from a first side of the base 112 and the second arm 116 extends from a second side of the base 112. The arms 114, 116 may be spaced apart from each other and extend away from the base 112 parallel to each other. A channel 118 may extend through the head portion 110 between the first arm 114 and the second arm 116. The channel 118 may be, for example, configured and dimensioned or sized and shaped to receive a spinal rod (not shown). The rod may be coupled to at least two screws 100. The interior surfaces of the arms 114, 116 on the sides of the channel 118 may be, for example, flat or planar. The bottom of the channel 118 may be, for example, curved or arced to correspond to the shape of a rod. The exterior surfaces of the arms 114, 116 may be, for example, rounded, curved, or arced. The surface of the arms 114, 116 at the first end 102 of the screw 100 may be, for example, flat or planar.

The shaft 140 may include a first end 142 and a second end 144 opposite the first end 142. The first end 142 of the shaft 140 is coupled to and extends from the middle section 120, 160, 210, 260, 310, 360. The shaft 140 may include threads 146 along at least a portion between the first end 142 and the second end 144. In the depicted embodiments, the threads 146 extend from the first end 142 to the second end 144.

Referring now to FIGS. 1-10, the implantable screw 100 also includes a middle portion or middle section 120. The middle portion 120 includes a first end 122 and a second end 124 opposite the first end 122. The first end 122 of the middle section 120 couples to and extends away from the head portion 110. The second end 124 of the middle section 120 couples to and extends away from the first end 142 of the shaft 140. The first end 122 is connected to the second end 124 by members 126, 128. The members 126, 128 may include a first member 126 and a second member 128. The first member 126 may connect a first side of the first end 122 and a first side of the second end 124. The first member 126 may be, for example, curved or arced between the first end 122 and the second end 124. The first member 126 may have a convex curvature. The second member 128 may connect a second side of the first end 122 and a second side of the second end 124. The second member 128 may be, for example, curved or arced between the first end 122 and the second end 124. The second member 128 may have a convex curvature. The first member 126 and the second member 128 each curve inward towards each other. The first member 126 and the second member 128 may be, for example, spaced apart from each other forming a through hole 130. The channel 118 may extend through the screw 100 perpendicular to the through hole 130. The first member 126 may extend away from the head 110 between the first arm 114 and the second arm 116 on a first side. The second member 128 may extend away from the head 110 between the first arm 114 and the second arm 116 on a second side. The first member 126 may also include a first recess region 132 inset into an exterior surface of the first member 126. The second member 128 may also include a second recess region 134 inset into an exterior surface of the second member 128.

Referring now to FIGS. 11-20, an implantable screw 150 is shown including a head portion 110, a middle portion 160, and a shaft 140. The middle portion 160 includes a first end 162 and a second end 164 opposite the first end 162. The first end 162 of the middle section 160 couples to and extends away from the head portion 110. The second end 164 of the middle section 160 couples to and extends away from the first end 142 of the shaft 140. The first end 162 is connected to the second end 164 by members 166, 168. The members 166, 168 may include a first member 166 and a second member 168. The first member 166 may connect a first side of the first end 162 and a first side of the second end 164. The first member 166 may be, for example, curved or arced between the first end 162 and the second end 164. The first member 166 may have a convex curvature. The second member 168 may connect a second side of the first end 162 and a second side of the second end 164. The second member 168 may be, for example, curved or arced between the first end 162 and the second end 164. The second member 168 may have a convex curvature. The first member 166 and the second member 168 each curve inward towards each other. The first member 166 and the second member 168 may be, for example, spaced apart from each other forming a through hole 170. The channel 118 may extend through the screw 150 parallel to the through hole 170. The first member 166 may extend away from the head 110 parallel with the first arm 114. The second member 168 may extend away from the head 110 parallel with the second arm 116. The first member 166 may also include a first recess region 172 inset into an exterior surface of the first member 166. The second member 168 may also include a second recess region 174 inset into an exterior surface of the second member 168.

Referring now to FIGS. 21-30, an implantable screw 200 is shown including a head portion 110, a middle portion 210, and a shaft 140. The middle portion 210 includes a first end 212 and a second end 214 opposite the first end 212. The first end 212 of the middle section 210 couples to and extends away from the head portion 110. The second end 214 of the middle section 210 couples to and extends away from the first end 142 of the shaft 140. The first end 212 is connected to the second end 214 by members 216, 218. The members 216, 218 may include a first member 216 and a second member 218. The first member 216 may connect a first side of the first end 212 and a first side of the second end 214. The first member 216 may be, for example, curved or arced between the first end 212 and the second end 214. The first member 216 may have a concave curvature. The second member 218 may connect a second side of the first end 212 and a second side of the second end 214. The second member 218 may be, for example, curved or arced between the first end 212 and the second end 214. The second member 218 may have a concave curvature. The first member 216 and the second member 218 each curve outwards away from each other. The first and second members 216, 218 may form, for example, a ring or circular shape. The first member 216 and the second member 218 may be, for example, spaced apart from each other forming a through hole 220. The channel 118 of the head portion 110 may extend through the screw 200 perpendicular to the through hole 220. The first member 216 may extend away from the head 110 between the first arm 114 and the second arm 116 on a first side. The second member 218 may extend away from the head 110 between the first arm 114 and the second arm 116 on a second side. The first member 216 and the second member 218 extend beyond the exterior surface of the head portion 110 and the shaft 140.

Referring now to FIGS. 31-40, an implantable screw 250 is shown including a head portion 110, middle portion 260, and a shaft 140. The middle portion 260 includes a first end 262 and a second end 264 opposite the first end 262. The first end 262 of the middle section 260 couples to and extends away from the head portion 110. The second end 264 of the middle portion 260 couples to and extends away from the first end 142 of the shaft 140. The first end 262 is connected to the second end 264 by members 266, 268. The members 266, 268 may include a first member 266 and a second member 268. The first member 266 may connect a first side of the first end 262 and a first side of the second end 264. The first member 266 may be, for example, curved or arced between the first end 262 and the second end 264. The first member 266 may have a concave curvature. The second member 268 may connect a second side of the first end 262 and a second side of the second end 264. The second member 268 may be, for example, curved or arced between the first end 262 and the second end 264. The second member 268 may have a concave curvature. The first member 266 and the second member 268 each curve outwards away from each other. The first and second members 266, 268 may form, for example, a ring or circular shape. The first member 266 and the second member 268 may be, for example, spaced apart from each other forming a through hole 270. The channel 118 of the head portion 110 may extend through the screw 250 parallel to the through hole 270. The first member 266 may extend away from the head 110 parallel with the first arm 114. The second member 268 may extend away from the head 110 parallel with the second arm 116. The first member 266 and the second member 268 extend beyond the exterior surface of the head portion 110 and the shaft 140.

Referring now to FIGS. 31-40, an implantable screw 300 is shown including a head portion 110, a middle portion 310, and a shaft 140. The middle portion 310 includes a first end 312 and a second end 314 opposite the first end 312. The first end 312 of the middle section 310 couples to and extends away from the head portion 110. The second end 314 of the middle section 310 couples to and extends away from the first end 142 of the shaft 140. The first end 312 is connected to the second end 314 by members 316, 318. The members 316, 318 may include a first member 316 and a second member 318. The first member 316 may connect a first side of the first end 312 and a first side of the second end 314. The first member 316 may be, for example, curved or arced between the first end 312 and the second end 314. The first member 316 may have a concave curvature. The second member 318 may connect a second side of the first end 312 and a second side of the second end 314. The second member 318 may be, for example, curved or arced between the first end 312 and the second end 314. The second member 318 may have a concave curvature. The first member 316 and the second member 318 each curve outwards away from each other. The first and second members 316, 318 may form, for example, an oval shape. The first member 316 and the second member 318 may be, for example, spaced apart from each other forming a through hole 320. The channel 118 of the head portion 110 may extend through the screw 300 perpendicular to the through hole 320. The first member 316 may extend away from the head 110 between the first arm 114 and the second arm 116 on a first side. The second member 318 may extend away from the head 110 between the first arm 114 and the second arm 116 on a second side. Although not shown, the middle portion 310 may be rotated 90 degrees, such that the channel 118 of the head portion 110 may extend through the screw 300 parallel to the through hole 320. In the alternative embodiment, the first member 316 may extend away from the head 110 parallel with the first arm 114. The second member 318 may extend away from the head 110 parallel with the second arm 116. The exterior surface of the first member 316 and the second member 318 may extend parallel to the exterior portion of the head portion 110.

Referring now to FIGS. 51-58, an implantable screw 350 is shown including a head portion 110, a middle portion 360, and a shaft 140. The middle portion 360 includes a first end 362 and a second end 364 opposite the first end 362. The first end 362 of the middle section 360 couples to and extends away from the head portion 110. The second end 364 of the middle section 360 couples to and extends away from the first end 142 of the shaft 140. The first end 362 is connected to the second end 364 by a member 366. The member 366 may be, for example, curved or arced between the first end 362 and the second end 364. The first and second ends of the member 366 may be, for example, larger than the intermediate portion of the member 366. The member 366 may be, for example, a solid element that is approximately cylindrical in shape or approximately cuboid in shape.

Although the present disclosure focuses on use of the implants 100, 150, 200, 250, 300, 350 in a patient's spine, it is also contemplated that the implants 100, 150, 200, 250, 300, 350 may be used, for example, to connect any bone segments and/or to fill a bony defect that might result from trauma, tumor, infection, or another event. The bone segments may include bone segments of long bones, the ankle, and like bones, as would be known by one of ordinary skill in the art. When used with long bones and other non-vertebral bones the implants 100, 150, 200, 250, 300, 350 may be placed, for example, within the bone segments to assist with fusing the bone segments back together. The implants 100, 150, 200, 250, 300, 350 would be secured to each of the bone segments.

As may be recognized by those of ordinary skill in the art based on the teachings herein, numerous changes and modifications may be made to the above-described and other embodiments of the present disclosure without departing from the scope of the disclosure. The screws and other components of the screws and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the screws and systems may include more or fewer components or features than the embodiments as described and illustrated herein. For example, the components and features of FIGS. 1-10, FIGS. 11-20, FIGS. 21-30, FIGS. 31-40, FIGS. 41-50, and FIGS. 51-58 may all be used interchangeably and in alternative combinations as would be modified or altered by one of skill in the art. Accordingly, this detailed description of the currently-preferred embodiments is to be taken as illustrative, as opposed to limiting the invention.

Moreover, approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value. When introducing elements of various embodiments, the articles "a," "an," "the," and "said" are intended to mean that there are one or more of the elements. The terms "comprising," "including," and "having" are intended to be inclusive and mean that there may be additional elements other than the listed elements. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable. Any examples of operating parameters are not exclusive of other parameters of the disclosed embodiments. Components, aspects, features, con-figurations, arrangements, uses and the like described, illustrated or otherwise disclosed herein with respect to any particular embodiment may similarly be applied to any other embodiment disclosed herein.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. An implantable screw, comprising:

a head portion, wherein the head portion comprises:

a base member;

a first arm extending away from a first side of the base member; and a second arm extending away from a second side of the base member, wherein the first arm is spaced apart from the second arm;

a shaft; and a middle portion coupling the head portion to the shaft, the middle portion comprising:

a first member coupled to and extending between a first side of the head portion and the shaft, wherein a first end of the first member is coupled directly to a bottom surface of the head portion and a second end of the first member is coupled directly to a top surface of the shaft, wherein the first member has a convex curvature along a longitudinal axis of the implantable screw as the first member extends between the head portion and the shaft; and a second member coupled to and extending between a second side of the head portion and the shaft, wherein a first end of the second member is coupled directly to the bottom surface of the head portion and a second end of the second member is coupled directly to the top surface of the shaft, wherein the second member has a convex curvature along a longitudinal axis of the implantable screw as the second member extends between the head portion and the shaft;

wherein the first member is separate and spaced apart from the second member.

2. The implantable screw of claim 1, the middle portion further comprises:

a through hole extending through the middle portion between the first member and the second member and wherein the through hole has an elliptical shape in cross section.

3. The implantable screw of claim 2, wherein the head portion further comprises:

a channel extending between the first arm and the second arm, wherein the channel has a closed bottom end, and wherein the channel and the through hole are separate and distinct from each other.

4. The implantable screw of claim 3, wherein the first member of the middle portion is coupled between the first arm and the second arm of the head portion, and wherein the second member of the middle portion is coupled between the first arm and the second arm of the head portion.

5. The implantable screw of claim 3, wherein the first member of the middle portion is coupled directly below the first arm, and wherein the second member of the middle portion is coupled directly below the second arm.

6. The implantable screw of claim 2, wherein the head portion further comprises:

a channel extending between the first arm and the second arm.

7. The implantable screw of claim 6, wherein the through hole extends through the middle portion perpendicular to the channel of the head portion and an axis of the implantable screw.

8. The implantable screw of claim 6, wherein the through hole extends through the middle portion parallel to the channel of the head portion and an axis of the implantable screw.

9. The implantable screw of claim 2, wherein the first member has a concave curvature as the first member extends between the head portion and the shaft, and wherein the second member has a concave curvature as the second member extends between the head portion and the shaft.

10. The implantable screw of claim 9, wherein the head portion further comprises:

a channel extending between the first arm and the second arm, wherein the channel has a closed bottom end, and wherein the channel and the through hole are separate and distinct from each other.

11. The implantable screw of claim 10, wherein the first member of the middle portion is coupled between the first arm and the second arm of the head portion, and wherein the second member of the middle portion is coupled between the first arm and the second arm of the head portion.

12. The implantable screw of claim 11, wherein the through hole extends through the middle portion perpendicular to the channel of the head portion and an axis of the implantable screw.

13. The implantable screw of claim 11, wherein the through hole extends through the middle portion parallel to the channel of the head portion and an axis of the implantable screw.

14. The implantable screw of claim 10, wherein the first member of the middle portion is coupled directly below the first arm, and wherein the second member of the middle portion is coupled directly below the second arm.

15. The implantable screw of claim 9, wherein the first arm and the second arm form a circular shape.

16. The implantable screw of claim 9, wherein the first arm and the second arm form an oval shape.

17. The implantable screw of claim 1, wherein the first member further comprises:

a first recessed region inset into an exterior surface of the first member; and wherein the second member further comprises:

a second recessed region inset into an exterior surface of the second member.

18. A method for using at least one implantable screw, comprising:

inserting a first implantable screw into a first vertebrae, wherein the first implantable screw comprises:

a head portion;

a shaft; and a middle portion coupling the head portion to the shaft, the middle portion comprising:

a first member coupled to and extending between a first side of the head portion and the shaft, wherein a first end of the first member is coupled directly to a second end of the head portion and a second end of the first member is coupled directly to a first end of the shaft; and a second member coupled to and extending between a second side of the head portion and the shaft, wherein a first end of the second member is coupled directly to the second end of the head portion and a second end of the second member is coupled directly to the first end of the shaft;

inserting a second implantable screw into a second vertebrae;

attaching a rod into the first implantable screw and the second implantable screw; and applying a physiological load onto the first implantable screw and the second implantable screw to flex a middle section of each implantable screw and displace a proximal section relative to a distal section of each implantable screw.

19. An implantable screw, comprising:

a head portion;

a shaft; and a middle portion coupling the head portion to the shaft, the middle portion comprising:

a first member coupled to and extending between a first side of the head portion and the shaft, wherein a first end of the first member is coupled directly to a bottom surface of the head portion and a second end of the first member is coupled directly to a top surface of the shaft; and a second member coupled to and extending between a second side of the head portion and the shaft, wherein a first end of the second member is coupled directly to the bottom surface of the head portion and a second end of the second member is coupled directly to the top surface of the shaft;

wherein the first member and the second member extend beyond an exterior surface of the head portion and an exterior surface of the shaft in a direction perpendicular to a longitudinal axis of the implantable screw.

20. An implantable screw, comprising:

a head portion, comprising:

a base member;

a first arm extending away from a first side of the base member;

a second arm extending away from a second side of the base member, wherein the first arm is spaced apart from the second arm; and a channel extending between the first arm and the second arm;

a shaft; and a middle portion coupling the head portion to the shaft, the middle portion comprising:

a first member coupled to and extending between a first side of the head portion and the shaft, wherein a first end of the first member is coupled directly to a bottom surface of the head portion and a second end of the first member is coupled directly to a top surface of the shaft;

a second member coupled to and extending between a second side of the head portion and the shaft, wherein a first end of the second member is coupled directly to the bottom surface of the head portion and a second end of the second member is coupled directly to the top surface of the shaft; and a through hole extending through the middle portion between the first member and the second member and wherein the through hole has an elliptical shape in cross section.

21. The implantable screw of claim 20, wherein the through hole extends through the middle portion at least one of perpendicular and parallel to the channel of the head portion and an axis of the implantable screw.

22. An implantable screw, comprising:

a head portion, comprising:

a base member;

a first arm extending away from a first side of the base member; and a second arm extending away from a second side of the base member, wherein the first arm is spaced apart from the second arm;

a shaft; and a middle portion coupling the head portion to the shaft, the middle portion comprising:

a first member coupled to and extending between a first side of the head portion and the shaft, wherein a first end of the first member is coupled directly to a bottom surface of the head portion and a second end of the first member is coupled directly to a top surface of the shaft, wherein the first member has a concave curvature as the first member extends between the head portion and the shaft; and a second member coupled to and extending between a second side of the head portion and the shaft, wherein a first end of the second member is coupled directly to the bottom surface of the head portion and a second end of the second member is coupled directly to the top surface of the shaft, wherein the second member has a concave curvature as the second member extends between the head portion and the shaft; and a through hole extending through the middle portion between the first member and the second member and wherein the through hole has an elliptical shape in cross section.

23. The implantable screw of claim 22, wherein the head portion further comprises:

a channel extending between the first arm and the second arm, wherein the channel has a closed bottom end, and wherein the channel and the through hole are separate and distinct from each other;

wherein the first member of the middle portion is coupled between the first arm and the second arm of the head portion;

wherein the second member of the middle portion is coupled between the first arm and the second arm of the head portion; and wherein the through hole extends through the middle portion at least one of perpendicular and parallel to the channel of the head portion and an axis of the implantable screw.

* * * * *